(12) United States Patent
Beck et al.

(10) Patent No.: US 7,736,633 B2
(45) Date of Patent: *Jun. 15, 2010

(54) METHOD FOR ENHANCING EFFECTS OF COLORANTS AND CONDITIONERS

(75) Inventors: William A. Beck, Middletown, DE (US); John P. O'Brien, Oxford, PA (US); Hong Wang, Kennett Square, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 717 days.

This patent is subject to a terminal disclaimer.

(21) Appl. No.: 11/512,910

(22) Filed: Aug. 30, 2006

(65) Prior Publication Data

US 2007/0067924 A1 Mar. 29, 2007

Related U.S. Application Data

(60) Provisional application No. 60/721,329, filed on Sep. 28, 2005.

(51) Int. Cl.
*A61K 8/64* (2006.01)
*A61Q 5/12* (2006.01)
(52) U.S. Cl. .................................. 424/70.6; 424/70.14
(58) Field of Classification Search ................ 424/70.6, 424/70.14
See application file for complete search history.

(56) References Cited

U.S. PATENT DOCUMENTS

| | | | |
|---|---|---|---|
| 4,416,873 A | 11/1983 | Puchalski et al. | |
| 4,482,537 A | 11/1984 | El-Menshawy et al. | |
| 5,192,332 A | 3/1993 | Lang et al. | |
| 5,223,409 A | 6/1993 | Ladner et al. | |
| 5,403,484 A | 4/1995 | Ladner et al. | |
| 5,449,754 A | 9/1995 | Nishioka | |
| 5,480,971 A | 1/1996 | Houghten et al. | |
| 5,490,980 A | 2/1996 | Richardson et al. | |
| 5,571,698 A | 11/1996 | Ladner et al. | |
| 5,585,275 A | 12/1996 | Hudson et al. | |
| 5,597,386 A | 1/1997 | Igarashi et al. | |
| 5,639,603 A | 6/1997 | Dower et al. | |
| 5,801,226 A | 9/1998 | Cummins et al. | |
| 5,837,500 A | 11/1998 | Ladner et al. | |
| 6,013,250 A | 1/2000 | Cannell et al. | |
| 6,232,287 B1 | 5/2001 | Ruoslahti et al. | |
| 6,267,957 B1 | 7/2001 | Green et al. | |
| 6,280,747 B1 | 8/2001 | Philippe et al. | |
| 6,344,443 B1 | 2/2002 | Liu et al. | |
| 6,537,330 B1 | 3/2003 | Hoeffkes et al. | |
| 6,551,361 B1 | 4/2003 | Cornwell et al. | |
| 6,620,419 B1 | 9/2003 | Lintner | |
| 6,818,023 B2 | 11/2004 | Hoeffkes et al. | |
| 7,544,353 B2 * | 6/2009 | Huang et al. ............... | 424/70.6 |
| 2002/0098524 A1 | 7/2002 | Muttay et al. | |
| 2003/0152976 A1 | 8/2003 | Janssen et al. | |
| 2003/0185870 A1 | 10/2003 | Grinstaff et al. | |
| 2005/0008604 A1 * | 1/2005 | Schultz et al. ............ | 424/70.14 |
| 2005/0050656 A1 | 3/2005 | Huang et al. | |
| 2005/0226839 A1 | 10/2005 | Huang et al. | |
| 2005/0249682 A1 | 11/2005 | Buseman-William et al. | |
| 2006/0073111 A1 | 4/2006 | O'Brien et al. | |

FOREIGN PATENT DOCUMENTS

| | | |
|---|---|---|
| EP | 0 453 097 A2 | 10/1991 |
| JP | 02311412 A | 12/1990 |
| JP | 06065049 A | 3/1994 |
| JP | 08104614 A | 4/1996 |
| JP | 09003100 A | 1/1997 |
| JP | 2002363026 A | 12/2002 |
| WO | WO 00/48558 A1 | 8/2000 |
| WO | WO 01/07009 A1 | 2/2001 |
| WO | WO 01/45652 A1 | 6/2001 |
| WO | WO 01/79479 A2 | 10/2001 |
| WO | WO 02/065134 A2 | 8/2002 |
| WO | WO 03/031477 A1 | 4/2003 |
| WO | WO 03/102020 A2 | 12/2003 |
| WO | WO 2004/000257 A2 | 12/2003 |
| WO | WO 2004/048399 A2 | 6/2004 |
| WO | WO2005025505 A2 | 3/2005 |
| WO | WO2005117537 A2 | 12/2005 |
| WO | WO2006028503 A1 | 3/2006 |
| WO | WO2006094094 A2 | 9/2006 |

OTHER PUBLICATIONS

U.S. Appl. No. 60/737,042, filed Nov. 15, 2005, David J. Lowe et al.
S.G. Dixit et. al., Combinatorial Chemistry—Principles and Practices, Journal of Scientific & Industrial Research, 1998, vol. 57:173-183.
Ronald H. Hoess, Protein Design and Phage Display, Chem. Rev., 2001, vol. 101:3205-3218.
Todd C. Holmes, Novel Peptide-Based Biomaterial Scaffolds for Tissue Engineering, Trends in Biotechnology, 2002, vol. 20:16-21.
Sandra R. Whaley et. al., Selection of Peptides With Semiconductor Binding Specificity for Directed Nanocrystal Assembly, Nature, vol. 405:665-668.

(Continued)

*Primary Examiner*—Maryam Monshipouri

(57) ABSTRACT

Methods are provided for enhancing the longevity of the binding of various benefit agents to hair and skin. Applications of traditional and non-traditional colorants and conditioners to hair and skin are amended with compositions of hair or skin-binding peptides respectively. The presence of the hair or skin-binding peptide compositions act to increase the longevity of the applied colorant or conditioner on the hair or skin.

20 Claims, No Drawings

OTHER PUBLICATIONS

Marc S. Reisch, Ingredients Makers Take Lessons From Biotechnology to Mastermind the Lastest in Personal Care, C&EN Northeast News Bureau, 2002, pp. 16-21.

David J. Kemp et. al., Direct Immunoassay for Detecting *Escherichia coli* Colonies That Contain Polypeptides Encoded by Cloned DNA Segments, Proc. Natl. Acad. Sci., 1981, vol. 78:4520-4524.

Cheng-Ting Chien et. al., The Two-Hybird System: A Method to Identify and Clones Genes for Proteins That Interact With a Protein of Interest, Proc. Natl. Acad. Sci., 1991, vol. 88:9578-9582.

David M. Helfman et. al., Identification of Clones That Encode Chicken Tropomyosin by Direct Immunological Screening of a CDNA Expression Library, Proc. Natl. Acad. Sci., 1983, vol. 80:31-35.

Maria Dani, Biological Libraries, J. of Receptor & Signal Transduction Research, 2001, vol. 21:447-468.

Genencor International, Bio Conference, San Francisco, California, Jun. 8, 2004—Meeting Presentation, pp. 1-29.

Sandra R. Whaley et. al., Selection of Peptides With Semiconductor Binding Specificity for Directed Nanocrystal Assembly, Nature, vol. 405:665-668, 2000.

* cited by examiner

```
SEQUENCE LISTING

<160> NUMBER OF SEQ ID NOS: 74

<210> SEQ ID NO 1
<211> LENGTH: 12
<212> TYPE: PRT
<213> ORGANISM: Artificial Sequence
<220> FEATURE:
<223> OTHER INFORMATION: Hair-binding Peptide

<400> SEQUENCE: 1

Thr Pro Pro Glu Leu Leu His Gly Asp Pro Arg Ser
1               5                   10

<210> SEQ ID NO 2
<211> LENGTH: 7
<212> TYPE: PRT
<213> ORGANISM: Artificial Sequence
```

```
<220> FEATURE:
<223> OTHER INFORMATION: Hair-binding Peptide

<400> SEQUENCE: 2

Asn Thr Ser Gln Leu Ser Thr
1               5

<210> SEQ ID NO 3
<211> LENGTH: 8
<212> TYPE: PRT
<213> ORGANISM: Artificial Sequence
<220> FEATURE:
<223> OTHER INFORMATION: Hair-binding Peptide

<400> SEQUENCE: 3

Arg Thr Asn Ala Ala Asp His Pro
1               5

<210> SEQ ID NO 4
<211> LENGTH: 12
<212> TYPE: PRT
<213> ORGANISM: Artificial Sequence
<220> FEATURE:
<223> OTHER INFORMATION: Hair-binding Peptide

<400> SEQUENCE: 4

Arg Thr Asn Ala Ala Asp His Pro Ala Ala Val Thr
1               5                  10

<210> SEQ ID NO 5
<211> LENGTH: 12
<212> TYPE: PRT
<213> ORGANISM: Artificial Sequence
<220> FEATURE:
<223> OTHER INFORMATION: Hair-binding Peptide

<400> SEQUENCE: 5

Ile Pro Trp Trp Asn Ile Arg Ala Pro Leu Asn Ala
1               5                  10

<210> SEQ ID NO 6
<211> LENGTH: 7
<212> TYPE: PRT
<213> ORGANISM: Artificial Sequence
<220> FEATURE:
<223> OTHER INFORMATION: Hair-binding Peptide

<400> SEQUENCE: 6

Asp Leu Thr Leu Pro Phe His
1               5

<210> SEQ ID NO 7
<211> LENGTH: 12
<212> TYPE: PRT
<213> ORGANISM: Artificial Sequence
<220> FEATURE:
<223> OTHER INFORMATION: Skin-binding Peptide

<400> SEQUENCE: 7

Thr Pro Phe His Ser Pro Glu Asn Ala Pro Gly Ser
1               5                  10

<210> SEQ ID NO 8
<211> LENGTH: 12
<212> TYPE: PRT
<213> ORGANISM: Artificial Sequence
<220> FEATURE:
```

```
<223> OTHER INFORMATION: Empirically Generated Hair and Skin-Binding
      Peptide

<400> SEQUENCE: 8

Lys Arg Gly Arg His Lys Arg Pro Lys Arg His Lys
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Empirically Generated Hair and Skin-Binding
      Peptide

<400> SEQUENCE: 9

Arg Leu Leu Arg Leu Leu Arg
1               5

<210> SEQ ID NO 10
<211> LENGTH: 12
<212> TYPE: PRT
<213> ORGANISM: Artificial Sequence
<220> FEATURE:
<223> OTHER INFORMATION: Empirically Generated Hair and Skin-Binding
      Peptide

<400> SEQUENCE: 10

His Lys Pro Arg Gly Gly Arg Lys Lys Ala Leu His
1               5                   10

<210> SEQ ID NO 11
<211> LENGTH: 18
<212> TYPE: PRT
<213> ORGANISM: Artificial Sequence
<220> FEATURE:
<223> OTHER INFORMATION: Empirically Generated Hair and Skin-Binding
      Peptide

<400> SEQUENCE: 11

Lys Pro Arg Pro Pro His Gly Lys Lys His Arg Pro Lys His Arg Pro
1               5                   10                  15

Lys Lys

<210> SEQ ID NO 12
<211> LENGTH: 18
<212> TYPE: PRT
<213> ORGANISM: Artificial Sequence
<220> FEATURE:
<223> OTHER INFORMATION: Empirically Generated Hair and Skin-Binding
      Peptide

<400> SEQUENCE: 12

Arg Gly Arg Pro Lys Lys Gly His Gly Lys Arg Pro Gly His Arg Ala
1               5                   10                  15

Arg Lys

<210> SEQ ID NO 13
<211> LENGTH: 37
<212> TYPE: PRT
<213> ORGANISM: Artificial Sequence
<220> FEATURE:
<223> OTHER INFORMATION: Peptide Spacer

<400> SEQUENCE: 13

Thr Ser Thr Ser Lys Ala Ser Thr Thr Thr Ser Ser Lys Thr Thr
```

```
            1               5                   10                  15
Thr Thr Ser Ser Lys Thr Thr Thr Thr Ser Lys Thr Ser Thr Thr
                    20                  25                  30

Ser Ser Ser Ser Thr
            35

<210> SEQ ID NO 14
<211> LENGTH: 22
<212> TYPE: PRT
<213> ORGANISM: Artificial Sequence
<220> FEATURE:
<223> OTHER INFORMATION: Peptide Spacer

<400> SEQUENCE: 14

Gly Gln Gly Gly Tyr Gly Gly Leu Gly Ser Gln Gly Ala Gly Arg Gly
1               5                   10                  15

Gly Leu Gly Gly Gln Gly
            20

<210> SEQ ID NO 15
<211> LENGTH: 10
<212> TYPE: PRT
<213> ORGANISM: Artificial Sequence
<220> FEATURE:
<223> OTHER INFORMATION: Peptide Spacer

<400> SEQUENCE: 15

Gly Pro Gly Gly Tyr Gly Pro Gly Gln Gln
1               5                   10

<210> SEQ ID NO 16
<211> LENGTH: 67
<212> TYPE: PRT
<213> ORGANISM: Artificial Sequence
<220> FEATURE:
<223> OTHER INFORMATION: Multi-Copy Hair-Binding Peptide

<400> SEQUENCE: 16

Pro Asn Thr Ser Gln Leu Ser Thr Gly Gly Gly Arg Thr Asn Ala Ala
1               5                   10                  15

Asp His Pro Lys Cys Gly Gly Gly Asn Thr Ser Gln Leu Ser Thr Gly
            20                  25                  30

Gly Gly Arg Thr Asn Ala Ala Asp His Pro Lys Cys Gly Gly Gly Asn
        35                  40                  45

Thr Ser Gln Leu Ser Thr Gly Gly Gly Arg Thr Asn Ala Ala Asp His
    50                  55                  60

Pro Lys Cys
65

<210> SEQ ID NO 17
<211> LENGTH: 55
<212> TYPE: PRT
<213> ORGANISM: Artificial Sequence
<220> FEATURE:
<223> OTHER INFORMATION: Multi-Copy Hair-Binding Peptide

<400> SEQUENCE: 17

Pro Arg Thr Asn Ala Ala Asp His Pro Ala Ala Val Thr Gly Gly Gly
1               5                   10                  15

Cys Gly Gly Gly Arg Thr Asn Ala Ala Asp His Pro Ala Ala Val Thr
            20                  25                  30

Gly Gly Gly Cys Gly Gly Gly Arg Thr Asn Ala Ala Asp His Pro Ala
```

Ala Val Thr Gly Gly Gly Cys
    50              55

<210> SEQ ID NO 18
<211> LENGTH: 50
<212> TYPE: PRT
<213> ORGANISM: Artificial Sequence
<220> FEATURE:
<223> OTHER INFORMATION: Multi-Copy Hair-Binding Peptide

<400> SEQUENCE: 18

Pro Arg Thr Asn Ala Ala Asp His Pro Ala Val Thr Gly Gly Gly
1               5                   10                  15

Cys Gly Gly Gly Ile Pro Trp Trp Asn Ile Arg Ala Pro Leu Asn Ala
                20                  25                  30

Gly Gly Gly Cys Gly Gly Gly Asp Leu Thr Leu Pro Phe His Gly Gly
        35                  40                  45

Gly Cys
    50

<210> SEQ ID NO 19
<211> LENGTH: 82
<212> TYPE: PRT
<213> ORGANISM: Artificial Sequence
<220> FEATURE:
<223> OTHER INFORMATION: Multi-Copy Hair-Binding Peptide

<400> SEQUENCE: 19

Pro Arg Thr Asn Ala Ala Asp His Pro Gly Gly Gly Thr Pro Pro Glu
1               5                   10                  15

Leu Leu His Gly Asp Pro Arg Ser Lys Cys Gly Gly Gly Arg Thr Asn
                20                  25                  30

Ala Ala Asp His Pro Gly Gly Gly Thr Pro Pro Glu Leu Leu His Gly
        35                  40                  45

Asp Pro Arg Ser Lys Cys Gly Gly Gly Arg Thr Asn Ala Ala Asp His
    50                  55                  60

Pro Gly Gly Gly Thr Pro Pro Glu Leu Leu His Gly Asp Pro Arg Ser
65                  70                  75                  80

Lys Cys

<210> SEQ ID NO 20
<211> LENGTH: 82
<212> TYPE: PRT
<213> ORGANISM: Artificial Sequence
<220> FEATURE:
<223> OTHER INFORMATION: Multi-Copy Hair-Binding Peptide

<400> SEQUENCE: 20

Pro Thr Pro Pro Thr Asn Val Leu Met Leu Ala Thr Lys Gly Gly Gly
1               5                   10                  15

Arg Thr Asn Ala Ala Asp His Pro Lys Cys Gly Gly Gly Thr Pro Pro
                20                  25                  30

Thr Asn Val Leu Met Leu Ala Thr Lys Gly Gly Gly Arg Thr Asn Ala
        35                  40                  45

Ala Asp His Pro Lys Cys Gly Gly Gly Thr Pro Pro Thr Asn Val Leu
    50                  55                  60

Met Leu Ala Thr Lys Gly Gly Gly Arg Thr Asn Ala Ala Asp His Pro
65                  70                  75                  80

-continued

Lys Cys

<210> SEQ ID NO 21
<211> LENGTH: 82
<212> TYPE: PRT
<213> ORGANISM: Artificial Sequence
<220> FEATURE:
<223> OTHER INFORMATION: Multi-Copy Hair-Binding Peptide

<400> SEQUENCE: 21

```
Pro Arg Thr Asn Ala Ala Asp His Pro Gly Gly Gly Thr Pro Pro Thr
1               5                   10                  15

Asn Val Leu Met Leu Ala Thr Lys Lys Cys Gly Gly Gly Arg Thr Asn
            20                  25                  30

Ala Ala Asp His Pro Gly Gly Gly Thr Pro Pro Thr Asn Val Leu Met
        35                  40                  45

Leu Ala Thr Lys Lys Cys Gly Gly Gly Arg Thr Asn Ala Ala Asp His
    50                  55                  60

Pro Gly Gly Gly Thr Pro Pro Thr Asn Val Leu Met Leu Ala Thr Lys
65                  70                  75                  80

Lys Cys
```

<210> SEQ ID NO 22
<211> LENGTH: 17
<212> TYPE: PRT
<213> ORGANISM: Artificial Sequence
<220> FEATURE:
<223> OTHER INFORMATION: Random Peptide Sequence

<400> SEQUENCE: 22

```
Lys Ser Lys Pro Tyr Pro Tyr Pro Pro Leu Pro Val Arg Pro Trp
1               5                   10                  15

Thr
```

<210> SEQ ID NO 23
<211> LENGTH: 230
<212> TYPE: DNA
<213> ORGANISM: Artificial Sequence
<220> FEATURE:
<223> OTHER INFORMATION: Coding Sequence for Multi-Copy Hair-Binding
      Peptide HC77607

<400> SEQUENCE: 23

```
ggatccgatc cgaacaccag tcagctgagt accggcggcg ccgcaccaa cgccgcggat      60 catccgaaat gtggcggcgg caacaccagc cagctgagca ccggtggcgg ccgtaccaat    120
gcggcggata tccgaaatg tggtggtggc aatacctctc agctgagcac gggcggcggc    180
cgtaccaatg ccgcggatca tccgaaatgc taataaggcg cgccaagctt              230
```

<210> SEQ ID NO 24
<211> LENGTH: 68
<212> TYPE: PRT
<213> ORGANISM: Artificial Sequence
<220> FEATURE:
<223> OTHER INFORMATION: TBP1 Peptide

<400> SEQUENCE: 24

```
Gly Ser Ile Glu Gly Arg Phe His Glu Asn Trp Pro Ser Gly Gly Gly
1               5                   10                  15

Thr Ser Thr Ser Lys Ala Ser Thr Thr Thr Thr Ser Ser Lys Thr Thr
            20                  25                  30
```

```
Thr Thr Ser Ser Lys Thr Thr Thr Thr Ser Lys Thr Ser Thr Thr
        35                  40                  45
Ser Ser Ser Ser Thr Gly Gly Gly Thr His Lys Thr Ser Thr Gln Arg
    50                  55                  60

Leu Leu Ala Ala
65

<210> SEQ ID NO 25
<211> LENGTH: 103
<212> TYPE: DNA
<213> ORGANISM: Artificial Sequence
<220> FEATURE:
<223> OTHER INFORMATION: Oligonucleotide TBP(+)1

<400> SEQUENCE: 25
ggatccatcg aaggtcgttt ccacgaaaac tggccgtctg gtggcggtac ctctacttcc      60
aaagcttcca ccactacgac ttctagcaaa accaccacta cat                      103

<210> SEQ ID NO 26
<211> LENGTH: 104
<212> TYPE: DNA
<213> ORGANISM: Artificial Sequence
<220> FEATURE:
<223> OTHER INFORMATION: Oligonulceotide TBP(+)2

<400> SEQUENCE: 26
cctctaagac taccacgact acctccaaaa cctctactac ctctagctcc tctacgggcg      60
gtggcactca caagacctct actcagcgtc tgctggctgc ataa                     104

<210> SEQ ID NO 27
<211> LENGTH: 69
<212> TYPE: DNA
<213> ORGANISM: Artificial Sequence
<220> FEATURE:
<223> OTHER INFORMATION: Oligonucleotide TBP(-)1

<400> SEQUENCE: 27
ttatgcagcc agcagacgct gagtagaggt cttgtgagtg ccaccgcccg tagaggagct      60
agaggtagt                                                             69

<210> SEQ ID NO 28
<211> LENGTH: 69
<212> TYPE: DNA
<213> ORGANISM: Artificial Sequence
<220> FEATURE:
<223> OTHER INFORMATION: Oligonucleotide TBP(-)2

<400> SEQUENCE: 28
agaggttttg gaggtagtcg tggtagtctt agaggatgta gtggtggttt tgctagaagt      60
cgtagtggt                                                             69

<210> SEQ ID NO 29
<211> LENGTH: 69
<212> TYPE: DNA
<213> ORGANISM: Artificial Sequence
<220> FEATURE:
<223> OTHER INFORMATION: Oligonucleotide TBP(-)3

<400> SEQUENCE: 29
ggaagctttg gaagtagagg taccgccacc agacggccag ttttcgtgga acgaccttc      60 gatggatcc                                                             69
```

<210> SEQ ID NO 30
<211> LENGTH: 207
<212> TYPE: DNA
<213> ORGANISM: Artificial Sequence
<220> FEATURE:
<223> OTHER INFORMATION: Synthetic DNA Fragment TBP1

<400> SEQUENCE: 30

```
ggatccatcg aaggtcgttt ccacgaaaac tggccgtctg ccggcggtac ctctacttcc      60
aaagcttcca ccactacgac ttctagcaaa accaccacta catcctctaa gactaccacg     120
actacctcca aaacctctac tacctctagc tcctctacgg gcggcgccac tcacaagacc     180
tctactcagc gtctgctggc tgcataa                                         207
```

<210> SEQ ID NO 31
<211> LENGTH: 22
<212> TYPE: DNA
<213> ORGANISM: Artificial Sequence
<220> FEATURE:
<223> OTHER INFORMATION: Primer

<400> SEQUENCE: 31

```
caccggatcc atcgaaggtc gt                                               22
```

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32

```
tcattatgca gccagcagcg c                                                21
```

<210> SEQ ID NO 33
<211> LENGTH: 35
<212> TYPE: DNA
<213> ORGANISM: Artificial Sequence
<220> FEATURE:
<223> OTHER INFORMATION: Primer

<400> SEQUENCE: 33

```
gaaaactggc cgtctgccgg cggtacctct acttc                                 35
```

<210> SEQ ID NO 34
<211> LENGTH: 35
<212> TYPE: DNA
<213> ORGANISM: Artificial Sequence
<220> FEATURE:
<223> OTHER INFORMATION: Primer

<400> SEQUENCE: 34

```
gaagtagagg taccgccggc agacggccag ttttc                                 35
```

<210> SEQ ID NO 35
<211> LENGTH: 33
<212> TYPE: DNA
<213> ORGANISM: Artificial Sequence
<220> FEATURE:
<223> OTHER INFORMATION: Primer

<400> SEQUENCE: 35

```
ctcctctacg gcggcgcca ctcacaagac ctc                                    33
```

<210> SEQ ID NO 36
<211> LENGTH: 33
<212> TYPE: DNA
<213> ORGANISM: Artificial Sequence
<220> FEATURE:
<223> OTHER INFORMATION: Primer

<400> SEQUENCE: 36

```
gaggtcttgt gagtggcgcc gcccgtagag gag                         33
```

<210> SEQ ID NO 37
<211> LENGTH: 68
<212> TYPE: PRT
<213> ORGANISM: Artificial Sequence
<220> FEATURE:
<223> OTHER INFORMATION: TBP101 Peptide

<400> SEQUENCE: 37

Gly Ser Ile Glu Gly Arg Phe His Glu Asn Trp Pro Ser Ala Gly Gly
1               5                   10                  15

Thr Ser Thr Ser Lys Ala Ser Thr Thr Thr Ser Ser Lys Thr Thr
            20                  25                  30

Thr Thr Ser Ser Lys Thr Thr Thr Thr Ser Lys Thr Ser Thr Thr
        35                  40                  45

Ser Ser Ser Ser Thr Gly Gly Ala Thr His Lys Thr Ser Thr Gln Arg
    50                  55                  60

Leu Leu Ala Ala
65

<210> SEQ ID NO 38
<211> LENGTH: 312
<212> TYPE: DNA
<213> ORGANISM: Artificial Sequence
<220> FEATURE:
<223> OTHER INFORMATION: Coding Sequence for INK101

<400> SEQUENCE: 38

```
catatgtcgt actaccatca ccatcaccat cacctcgaat caacaagttt gtacaaaaaa     60
gcaggctccg cggccgcccc cttcaccgga tccatcgaag gtcgtttcca cgaaaactgg    120
ccgtctgccg gcggtacctc tacttccaaa gcttccacca ctacgacttc tagcaaaacc    180
accactacat cctctaagac taccacgact acctccaaaa cctctactac ctctagctcc    240
tctacgggcg gcgccactca caagacctct actcagcgtc tgctggctgc ataatgaaag    300
ggtgggcgcg cc                                                        312
```

<210> SEQ ID NO 39
<211> LENGTH: 96
<212> TYPE: PRT
<213> ORGANISM: Artificial Sequence
<220> FEATURE:
<223> OTHER INFORMATION: TBP101-DP Peptide

<400> SEQUENCE: 39

Met Ser Tyr Tyr His His His His His His Leu Glu Ser Thr Ser Leu
1               5                   10                  15

Tyr Lys Lys Ala Gly Ser Ala Ala Ala Pro Phe Thr Gly Ser Ile Asp
            20                  25                  30

Pro Arg Phe His Glu Asn Trp Pro Ser Ala Gly Gly Thr Ser Thr Ser
        35                  40                  45

Lys Ala Ser Thr Thr Thr Ser Ser Lys Thr Thr Thr Thr Ser Ser
    50                  55                  60

Lys Thr Thr Thr Thr Thr Ser Lys Thr Ser Thr Ser Ser Ser Ser
65                  70                  75                  80

Thr Gly Gly Ala Thr His Lys Thr Ser Thr Gln Arg Leu Leu Ala Ala
            85                  90                  95

<210> SEQ ID NO 40
<211> LENGTH: 45
<212> TYPE: DNA
<213> ORGANISM: Artificial Sequence
<220> FEATURE:
<223> OTHER INFORMATION: Oligonucleotide used in site-directed
      mutagenesis

<400> SEQUENCE: 40
cccctccacc ggatccatcg atccacgttt ccacgaaaac tggcc            45

<210> SEQ ID NO 41
<211> LENGTH: 45
<212> TYPE: DNA
<213> ORGANISM: Artificial Sequence
<220> FEATURE:
<223> OTHER INFORMATION: Oligonucleotide used in site-directed
      mutangenesis

<400> SEQUENCE: 41
ggccagtttt cgtggaaacg tggatcgatg gatccggtga agggg             45

<210> SEQ ID NO 42
<211> LENGTH: 4945
<212> TYPE: DNA
<213> ORGANISM: Artificial Sequence
<220> FEATURE:
<223> OTHER INFORMATION: pINK101-DP Plasmid

<400> SEQUENCE: 42
agatctcgat cccgcgaaat taatacgact cactataggg agaccacaac ggtttccctc    60
tagaaataat tttgtttaac tttaagaagg agatatacat atgtcgtact accatcacca   120
tcaccatcac ctcgaatcaa caagtttgta caaaaaagca ggctccgcgg ccgcccccctt   180 caccggatcc atcgatccac gtttccacga aaactggccg tctgccggcg gtacctctac   240
ttccaaagct tccaccacta cgacttctag caaaaccacc actacatcct ctaagactac   300
cacgactacc tccaaaacct ctactacctc tagctcctct acgggcggcg ccactcacaa   360
gacctctact cagcgtctgc tggctgcata atgaaaggt gggcgcgccg acccagcttt   420
cttgtacaaa gtggttgatt cgaggctgct aacaaagccc gaaaggaagc tgagttggct   480
gctgccaccg ctgagcaata actagcataa ccccttgggg cctctaaacg ggtcttgagg   540
ggttttttgc tgaaaggagg aactatatcc ggatatccac aggacgggtg tggtcgccat   600
gatcgcgtag tcgatagtgg ctccaagtag cgaagcgagc aggactgggc ggcggccaaa   660
gcggtcggac agtgctccga aacgggtgc gcatagaaat tgcatcaacg catatagcgc   720
tagcagcacg ccatagtgac tggcgatgct gtcggaatgg acgatatccc gcaagaggcc   780
cggcagtacc ggcataacca agcctatgcc tacagcatcc agggtgacgg tgccgaggat   840
gacgatgagc gcattgttag atttcataca cggtgcctga ctgcgttagc aatttaactg   900
tgataaacta ccgcattaaa gcttatcgat gataagctgt caaacatgag aattcttgaa   960
gacgaaaggg cctcgtgata cgcctatttt tataggttaa tgtcatgata ataatggttt   1020
cttagacgtc aggtggcact tttcggggaa atgtgcgcgg aacccctatt tgtttatttt   1080

-continued

```
tctaaataca ttcaaatatg tatccgctca tgagacaata accctgataa atgcttcaat      1140
aatattgaaa aaggaagagt atgagtattc aacatttccg tgtcgccctt attccctttt      1200
ttgcggcatt ttgccttcct gttttttgctc acccagaaac gctggtgaaa gtaaaagatg     1260
ctgaagatca gttgggtgca cgagtgggtt acatcgaact ggatctcaac agcggtaaga     1320
tccttgagag ttttcgcccc gaagaacgtt ttccaatgat gagcactttt aaagttctgc      1380
tatgtggcgc ggtattatcc cgtgttgacg ccgggcaaga gcaactcggt cgccgcatac     1440
actattctca gaatgacttg gttgagtact caccagtcac agaaaagcat cttacggatg     1500
gcatgacagt aagagaatta tgcagtgctg ccataaccat gagtgataac actgcggcca    1560
acttacttct gacaacgatc ggaggaccga aggagctaac cgcttttttg cacaacatgg    1620
gggatcatgt aactcgcctt gatcgttggg aaccggagct gaatgaagcc ataccaaacg    1680
acgagcgtga caccacgatg cctgcagcaa tggcaacaac gttgcgcaaa ctattaactg    1740
gcgaactact tactctagct tcccggcaac aattaataga ctggatggag gcggataaag    1800
ttgcaggacc acttctgcgc tcggcccttc cggctggctg gtttattgct gataaatctg    1860
gagccggtga gcgtgggtct cgcggtatca ttgcagcact ggggccagat ggtaagccct    1920
cccgtatcgt agttatctac acgacgggga gtcaggcaac tatggatgaa cgaaatagac    1980
agatcgctga gataggtgcc tcactgatta agcattggta actgtcagac caagtttact    2040
catatatact ttagattgat ttaaaacttc attttaatt taaaaggatc taggtgaaga    2100
tcctttttga taatctcatg accaaaatcc cttaacgtga gttttcgttc cactgagcgt    2160 cagacccgt agaaaagatc aaaggatctt cttgagatcc ttttttttctg cgcgtaatct    2220 gctgcttgca acaaaaaaa ccaccgctac cagcggtggt ttgtttgccg gatcaagagc    2280
taccaactct ttttccgaag gtaactggct tcagcagagc gcagatacca aatactgtcc    2340
ttctagtgta gccgtagtta ggccaccact tcaagaactc tgtagcaccg cctacatacc    2400
tcgctctgct aatcctgtta ccagtggctg ctgccagtgg cgataagtcg tgtcttaccg    2460
ggttggactc aagacgatag ttaccggata aggcgcagcg gtcgggctga acgggggggtt    2520 cgtgcacaca gcccagcttg gagcgaacga cctacaccga actgagatac ctacagcgtg    2580
agctatgaga aagcgccacg cttcccgaag ggagaaaggc ggacaggtat ccggtaagcg    2640
gcagggtcgg aacaggagag cgcacgaggg agcttccagg gggaaacgcc tggtatcttt    2700
atagtcctgt cgggtttcgc cacctctgac ttgagcgtcg attttttgtga tgctcgtcag    2760 gggggcggag cctatggaaa aacgccagca acgcggcctt tttacggttc ctggccttttt    2820 gctggccttt tgctcacatg ttctttcctg cgttatcccc tgattctgtg gataaccgta    2880
ttaccgcctt tgagtgagct gataccgctc gccgcagccg aacgaccgag cgcagcgagt    2940
cagtgagcga ggaagcggaa gagcgcctga tgcggtattt tctccttacg catctgtgcg    3000
gtatttcaca ccgcatatat ggtgcactct cagtacaatc tgctctgatg ccgcatagtt    3060
aagccagtat acactccgct atcgctacgt gactgggtca tggctgcgcc ccgacacccg    3120
ccaacacccg ctgacgcgcc ctgacgggct tgtctgctcc cggcatccgc ttacagacaa    3180
gctgtgaccg tctccgggag ctcatgtgt cagaggtttt caccgtcatc accgaaacgc    3240
gcgaggcagc tgcggtaaag ctcatcagcg tggtcgtgaa gcgattcaca gatgtctgcc    3300
tgttcatccg cgtccagctc gttgagtttc tccagaagcg ttaatgtctg gcttctgata    3360
aagcgggcca tgttaagggc ggttttttcc tgtttggtca ctgatgcctc cgtgtaaggg    3420
ggatttctgt tcatggggt aatgataccg atgaaacgag agaggatgct cacgatacgg    3480
```

-continued

```
gttactgatg atgaacatgc ccggttactg aacgttgtg agggtaaaca actggcggta      3540
tggatgcggc gggaccagag aaaaatcact cagggtcaat gccagcgctt cgttaataca      3600
gatgtaggtg ttccacaggg tagccagcag catcctgcga tgcagatccg aacataatg      3660 gtgcagggcg ctgacttccg cgtttccaga ctttacgaaa cacggaaacc gaagaccatt      3720
catgttgttg ctcaggtcgc agacgttttg cagcagcagt cgcttcacgt tcgctcgcgt      3780
atcggtgatt cattctgcta accagtaagg caaccccgcc agcctagccg ggtcctcaac      3840
gacaggagca cgatcatgcg cacccgtggc caggacccaa cgctgcccga tgcgccgc       3900 gtgcggctgc tggagatggc ggacgcgatg gatatgttct gccaagggtt ggtttgcgca      3960
ttcacagttc tccgcaagaa ttgattggct ccaattcttg gagtggtgaa tccgttagcg      4020
aggtgccgcc ggcttccatt caggtcgagg tggcccggct ccatgcaccg cgacgcaacg      4080
cggggaggca gacaaggtat agggcggcgc ctacaatcca tgccaacccg ttccatgtgc      4140
tcgccgaggc ggcataaatc gccgtgacga tcagcggtcc agtgatcgaa gttaggctgg      4200
taagagccgc gagcgatcct tgaagctgtc cctgatggtc gtcatctacc tgcctggaca      4260
gcatggcctg caacgcgggc atcccgatgc cgccggaagc gagaagaatc ataatgggga      4320
aggccatcca gcctcgcgtc gcgaacgcca gcaagacgta gcccagcgcg tcggccgcca      4380
tgccggcgat aatggcctgc ttctcgccga aacgtttggt ggcgggacca gtgacgaagg      4440
cttgagcgag ggcgtgcaag attccgaata ccgcaagcga caggccgatc atcgtcgcgc      4500
tccagcgaaa gcggtcctcg ccgaaaatga cccagagcgc tgccggcacc tgtcctacga      4560
gttgcatgat aaagaagaca gtcataagtg cggcgacgat agtcatgccc cgcgcccacc      4620
ggaaggagct gactgggttg aaggctctca agggcatcgg tcgatcgacg ctctccctta      4680
tgcgactcct gcattaggaa gcagcccagt agtaggttga ggccgttgag caccgccgcc      4740
gcaaggaatg tgcatgcaa ggagatggcg cccaacagtc ccccggccac ggggcctgcc      4800
accataccca cgccgaaaca agcgctcatg agcccgaagt ggcgagcccg atcttcccca      4860
tcggtgatgt cggcgatata ggcgccagca accgcacctg tggcgccggt gatgccggcc      4920
acgatgcgtc cggcgtagag gatcg                                          4945
```

<210> SEQ ID NO 43
<211> LENGTH: 22
<212> TYPE: PRT
<213> ORGANISM: Artificial Sequence
<220> FEATURE:
<223> OTHER INFORMATION: IBT3 Peptide

<400> SEQUENCE: 43

Ser Arg Arg Pro Arg Gln Leu Gln Gln Arg Gln Ser Arg Arg Pro Arg
1               5                   10                  15

Gln Leu Gln Gln Arg Gln
            20

<210> SEQ ID NO 44
<211> LENGTH: 71
<212> TYPE: DNA
<213> ORGANISM: Artificial Sequence
<220> FEATURE:
<223> OTHER INFORMATION: Oligonucleotide used to make IBT3 peptide

<400> SEQUENCE: 44
tatgagccgt cgtccgcgtc agttgcagca gcgtcagagc cgtcgtccgc gtcagttgca      60
gcagcgtcag g                                                         71

<210> SEQ ID NO 45
<211> LENGTH: 73
<212> TYPE: DNA
<213> ORGANISM: Artificial Sequence
<220> FEATURE:
<223> OTHER INFORMATION: Oligonucleotide used to make IBT3 peptide

<400> SEQUENCE: 45
gatccctgac gctgctgcaa ctgacgcgga cgacggctct gacgctgctg caactgacgc     60
ggacgacggc tca                                                       73

<210> SEQ ID NO 46
<211> LENGTH: 49
<212> TYPE: DNA
<213> ORGANISM: Artificial Sequence
<220> FEATURE:
<223> OTHER INFORMATION: Primer

<400> SEQUENCE: 46
ccttaaggca tgtatgatgg atccctggca tgcgtgaata ttcttctcg                49

<210> SEQ ID NO 47
<211> LENGTH: 25
<212> TYPE: DNA
<213> ORGANISM: Artificial Sequence
<220> FEATURE:
<223> OTHER INFORMATION: Primer

<400> SEQUENCE: 47
gagcggataa caattcccct ctaga                                          25

<210> SEQ ID NO 48
<211> LENGTH: 39
<212> TYPE: DNA
<213> ORGANISM: Artificial Sequence
<220> FEATURE:
<223> OTHER INFORMATION: Oligonucleotide used in site-directed
      mutagenesis

<400> SEQUENCE: 48
gatgacgcca cggtggaaga acccgtgggt tccgagccc                           39

<210> SEQ ID NO 49
<211> LENGTH: 39
<212> TYPE: DNA
<213> ORGANISM: Artificial Sequence
<220> FEATURE:
<223> OTHER INFORMATION: Oliginucleotide used in site-directed
      mutagenesis

<400> SEQUENCE: 49
gggctcggaa cccacgggtt cttccaccgt ggcgtcatc                           39

<210> SEQ ID NO 50
<211> LENGTH: 43
<212> TYPE: DNA
<213> ORGANISM: Artificial Sequence
<220> FEATURE:
<223> OTHER INFORMATION: Oligonucleotide used in site-directed
      mutagenesis

<400> SEQUENCE: 50
ggcgagaaga atattcacgc atcccaggga tccatcgatc cac                      43

<210> SEQ ID NO 51
<211> LENGTH: 43
<212> TYPE: DNA
<213> ORGANISM: Artificial Sequence
<220> FEATURE:
<223> OTHER INFORMATION: Oligonucleotide used in site-directed
      mutagenesis

<400> SEQUENCE: 51
gtggatcgat ggatccctgg gatgcgtgaa tattcttctc gcc                    43

<210> SEQ ID NO 52
<211> LENGTH: 13
<212> TYPE: PRT
<213> ORGANISM: Artificial Sequence
<220> FEATURE:
<223> OTHER INFORMATION: Hair-binding peptide haveing a cysteine residue
      added to the C-terminus

<400> SEQUENCE: 52

Thr Pro Pro Glu Leu Leu His Gly Asp Pro Arg Ser Cys
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Hair-Binding Peptide

<400> SEQUENCE: 53

Glu Gln Ile Ser Gly Ser Leu Val Ala Ala Pro Trp
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Hair-Binding Peptide

<400> SEQUENCE: 54

Thr Asp Met Gln Ala Pro Thr Lys Ser Tyr Ser Asn
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Hair-Binding Peptide

<400> SEQUENCE: 55

Ala Leu Pro Arg Ile Ala Asn Thr Trp Ser Pro Ser
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Hair-Binding Peptide

<400> SEQUENCE: 56

Leu Asp Thr Ser Phe Pro Pro Val Pro Phe His Ala
1               5                   10

```
<210> SEQ ID NO 57
<211> LENGTH: 12
<212> TYPE: PRT
<213> ORGANISM: Artificial Sequence
<220> FEATURE:
<223> OTHER INFORMATION: Hair-Binding Peptide

<400> SEQUENCE: 57

Thr Pro Pro Thr Asn Val Leu Met Leu Ala Thr Lys
1               5                   10

<210> SEQ ID NO 58
<211> LENGTH: 15
<212> TYPE: PRT
<213> ORGANISM: Artificial Sequence
<220> FEATURE:
<223> OTHER INFORMATION: Hair-Binding Peptide

<400> SEQUENCE: 58

Ser Thr Leu His Lys Tyr Lys Ser Gln Asp Pro Thr Pro His His
1               5                   10                  15

<210> SEQ ID NO 59
<211> LENGTH: 12
<212> TYPE: PRT
<213> ORGANISM: Artificial Sequence
<220> FEATURE:
<223> OTHER INFORMATION: Hair-Binding Peptide

<400> SEQUENCE: 59

Gly Met Pro Ala Met His Trp Ile His Pro Phe Ala
1               5                   10

<210> SEQ ID NO 60
<211> LENGTH: 15
<212> TYPE: PRT
<213> ORGANISM: Artificial Sequence
<220> FEATURE:
<223> OTHER INFORMATION: Hair-Binding Peptide

<400> SEQUENCE: 60

His Asp His Lys Asn Gln Lys Glu Thr His Gln Arg His Ala Ala
1               5                   10                  15

<210> SEQ ID NO 61
<211> LENGTH: 20
<212> TYPE: PRT
<213> ORGANISM: Artificial Sequence
<220> FEATURE:
<223> OTHER INFORMATION: Hair-Binding Peptide

<400> SEQUENCE: 61

His Asn His Met Gln Glu Arg Tyr Thr Asp Pro Gln His Ser Pro Ser
1               5                   10                  15

Val Asn Gly Leu
            20

<210> SEQ ID NO 62
<211> LENGTH: 20
<212> TYPE: PRT
<213> ORGANISM: Artificial Sequence
<220> FEATURE:
<223> OTHER INFORMATION: Hair-Binding Peptide

<400> SEQUENCE: 62

Thr Ala Glu Ile Gln Ser Ser Lys Asn Pro Asn Pro His Pro Gln Arg
```

```
                    1               5                  10                 15

Ser Trp Thr Asn
             20

<210> SEQ ID NO 63
<211> LENGTH: 12
<212> TYPE: PRT
<213> ORGANISM: Artificial Sequence
<220> FEATURE:
<223> OTHER INFORMATION: Skin-Binding Peptide

<400> SEQUENCE: 63

Thr Met Gly Phe Thr Ala Pro Arg Phe Pro His Tyr
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Skin-Binding Peptide

<400> SEQUENCE: 64

Ser Val Ser Val Gly Met Lys Pro Ser Pro Arg Pro
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Skin-Binding Peptide

<400> SEQUENCE: 65

Asn Leu Gln His Ser Val Gly Thr Ser Pro Val Trp
1               5                   10

<210> SEQ ID NO 66
<211> LENGTH: 15
<212> TYPE: PRT
<213> ORGANISM: Artificial Sequence
<220> FEATURE:
<223> OTHER INFORMATION: Skin-Binding Peptide

<400> SEQUENCE: 66

Gln Leu Ser Tyr His Ala Tyr Pro Gln Ala Asn His His Ala Pro
1               5                   10                  15

<210> SEQ ID NO 67
<211> LENGTH: 14
<212> TYPE: PRT
<213> ORGANISM: Artificial Sequence
<220> FEATURE:
<223> OTHER INFORMATION: Skin-Binding Peptide

<400> SEQUENCE: 67

Ser Gly Cys His Leu Val Tyr Asp Asn Gly Phe Cys Asp His
1               5                   10

<210> SEQ ID NO 68
<211> LENGTH: 14
<212> TYPE: PRT
<213> ORGANISM: Artificial Sequence
<220> FEATURE:
<223> OTHER INFORMATION: Skin-Binding Peptide

<400> SEQUENCE: 68
```

-continued

```
Ala Ser Cys Pro Ser Ala Ser His Ala Asp Pro Cys Ala His
1               5                   10
```

<210> SEQ ID NO 69
<211> LENGTH: 14
<212> TYPE: PRT
<213> ORGANISM: Artificial Sequence
<220> FEATURE:
<223> OTHER INFORMATION: Skin-Binding Peptide

<400> SEQUENCE: 69

```
Asn Leu Cys Asp Ser Ala Arg Asp Ser Pro Arg Cys Lys Val
1               5                   10
```

<210> SEQ ID NO 70
<211> LENGTH: 12
<212> TYPE: PRT
<213> ORGANISM: Artificial Sequence
<220> FEATURE:
<223> OTHER INFORMATION: Skin-Binding Peptide

<400> SEQUENCE: 70

```
Asn His Ser Asn Trp Lys Thr Ala Ala Asp Phe Leu
1               5                   10
```

<210> SEQ ID NO 71
<211> LENGTH: 12
<212> TYPE: PRT
<213> ORGANISM: Artificial Sequence
<220> FEATURE:
<223> OTHER INFORMATION: Skin-Binding Peptide

<400> SEQUENCE: 71

```
Ser Asp Thr Ile Ser Arg Leu His Val Ser Met Thr
1               5                   10
```

<210> SEQ ID NO 72
<211> LENGTH: 12
<212> TYPE: PRT
<213> ORGANISM: Artificial Sequence
<220> FEATURE:
<223> OTHER INFORMATION: Skin-Binding Peptide

<400> SEQUENCE: 72

```
Ser Pro Tyr Pro Ser Trp Ser Thr Pro Ala Gly Arg
1               5                   10
```

<210> SEQ ID NO 73
<211> LENGTH: 14
<212> TYPE: PRT
<213> ORGANISM: Artificial Sequence
<220> FEATURE:
<223> OTHER INFORMATION: Skin-Binding Peptide

<400> SEQUENCE: 73

```
Asp Ala Cys Ser Gly Asn Gly His Pro Asn Asn Cys Asp Arg
1               5                   10
```

<210> SEQ ID NO 74
<211> LENGTH: 14

```
<212> TYPE: PRT
<213> ORGANISM: Artificial Sequence
<220> FEATURE:
<223> OTHER INFORMATION: Skin-Binding Peptide

<400> SEQUENCE: 74

Asp Trp Cys Asp Thr Ile Ile Pro Gly Arg Thr Cys His Gly
1               5                   10
```

METHOD FOR ENHANCING EFFECTS OF COLORANTS AND CONDITIONERS

This patent application claims the benefit of U.S. Provisional Patent Application No. 60/721,329, filed Sep. 28, 2005.

FIELD OF THE INVENTION

The invention pertains to the field of personal care and particularly the treatment of hair and skin. More specifically, the invention provides a method for enhancing the effects of traditional and non-traditional colorants, conditioners, and other benefit agents with the application of a peptide-based sealant.

BACKGROUND OF THE INVENTION

Conditioners and colorants for hair and skin are well-known and frequently used personal care products. The major problem with current conditioners and non-oxidative colorants is that they lack the required durability for long-lasting effects. Oxidative hair dyes provide long-lasting color, but the oxidizing agents they contain cause hair damage. In order to improve the durability of hair and skin care compositions, peptide-based hair conditioners, hair colorants, and other benefit agents have been developed (Huang et al., copending and commonly owned U.S. Patent Application Publication No. 2005/0050656, and U.S. Patent Application Publication No. 2005/0226839). Peptide-based sunscreens have also been described (Buseman-Williams et al., copending and commonly owned U.S. Patent Application Publication No. 2005/0249682; and Lowe et al., copending and commonly owned U.S. patent application No. 60/737,042). The peptide-based benefit agents are prepared by coupling a specific peptide sequence that has a high binding affinity to hair or skin with a benefit agent, such as a conditioning or coloring agent. The peptide portion binds to the hair or skin, thereby strongly attaching the benefit agent. These peptide-based benefit agents provide improved durability, but require the coupling of the binding peptide to the benefit agent.

Peptides with a high binding affinity to hair have been identified using phage display screening techniques (Huang et al., supra; Estell et al. WO 0179479; Murray et al., U.S. Patent Application Publication No. 2002/0098524; Janssen et al., U.S. Patent Application Publication No. 2003/0152976; and Janssen et al., WO 04048399). Additionally, empirically generated hair and skin-binding peptides that are based on positively charged amino acids have been reported (Rothe et., WO 2004/000257).

Cornwell et al. (U.S. Pat. No. 6,551,361) describe a method for reducing color loss from hair treated with an oxidative hair dye comprising contacting the hair, either before or after treatment of the hair with the oxidative hair dye, with an organic amino compound, such as basic amino acids, urea, guanidine, and salts or mixtures thereof. However, that disclosure does not describe the use of specific hair-binding or skin-binding peptides, or conjugates comprising hair-binding or skin-binding peptides coupled to a benefit agent as sealants for colorants and conditioners.

The problem to be solved, therefore, is to provide alternative methods to enhance the durability of conditioners and colorants for hair and skin that are simple and easy to implement.

Applicants have addressed the stated problem by discovering that the effects of traditional and non-traditional colorants, conditioners, and other benefit agents are enhanced with the application of a peptide-based sealant.

SUMMARY OF THE INVENTION

The invention relates to new peptide based sealants useful for enhancing the longevity of traditional and non-traditional hair and skin colorants, conditioners, and other benefit agents. The sealants of the invention are short peptides, selected for their ability to specifically bind hair or skin. These hair-binding peptides (HBP) or skin-binding peptides (SBP) are applied in conjunction with a colorant, conditioner or some other benefit agent to hair or skin.

Accordingly the invention provides a method for applying a benefit agent to hair comprising the steps of:
  a) providing a hair benefit agent having affinity to hair;
  b) providing a composition comprising a hair-binding peptide;
  c) applying the benefit agent and the composition comprising a hair-binding peptide to hair for a time sufficient for the hair benefit agent and the hair-binding peptide to bind to hair.

Optionally, the composition comprising a hair-binding peptide may be reapplied as needed. In an alternate embodiment, the methods of the invention may also employ a polymer sealant to further enhance binding the benefit agent to the hair.

Similarly, the invention provides a method for applying a benefit agent to skin comprising the steps of:
  a) providing a skin benefit agent having affinity to skin;
  b) providing a composition comprising a skin-binding peptide;
  c) applying the benefit agent and the composition comprising a skin-binding peptide to skin for a time sufficient for the skin benefit agent and the skin-binding peptide to bind to skin.

Additionally, the invention provides a hair colorant composition comprising a hair colorant and a hair-binding peptide as well as a hair conditioning composition comprising a hair conditioner and a hair-binding peptide. Similarly, the invention provides a skin conditioning composition comprising a skin conditioner and a skin-binding peptide as well as a skin colorant composition comprising a skin colorant and a skin-binding peptide.

In a specific embodiment the invention provides a hair-binding peptide selected from the group consisting of SEQ ID NOs:16, 17, 18, 19, 20, and 21.

SEQUENCE DESCRIPTIONS

The various embodiments of the invention can be more fully understood from the following detailed description and the accompanying sequence descriptions, which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

A Sequence Listing is provided herewith on Compact Disk. The contents of the Compact Disk containing the Sequence Listing are hereby incorporated by reference in compliance with 37 CFR 1.52(e). The Compact Disks are submitted in triplicate and are identical to one another. The disks are labeled "Copy 1—Sequence Listing", "Copy 2—Sequence listing", and CRF. The disks contain the following file: CL3139 Seq Listing conv.ST25 having the following size: 29,000 bytes and which was created Aug. 29, 2006.

SEQ ID NOs:1-6 and 53-62 are the amino acid sequences of hair-binding peptides.

SEQ ID NO:7, and 63-74 are the amino acid sequence of a skin-binding peptides.

SEQ ID NOs:8-12 are the amino acid sequences of empirically generated hair and skin-binding peptides.

SEQ ID NOs:13-15 are the amino acid sequences of peptide spacers.

SEQ ID NOs:16-21 are the amino acid sequences of multi-copy hair-binding peptides.

SEQ ID NO:22 is the amino acid sequence of a random peptide.

SEQ ID NO:23 is the nucleic acid sequence of the coding region for multi-copy hair-binding peptide HC77607.

SEQ ID NO: 24 is the amino acid sequence of peptide TBP1.

SEQ ID NOs:25-29 are the nucleic acid sequences of oligonucleotides used to prepare the TBP1 gene, as described in Example 5.

SEQ ID NO:30 is the nucleic acid sequence of the synthetic DNA fragment TBP1.

SEQ ID NOs:31-36 are the nucleic acid sequences of oligonucleotide primers used to prepare the pINK1 expression plasmid, as described in Example 5.

SEQ ID NO:37 is the amino acid sequence of the TBP101 peptide described in Example 5.

SEQ ID NO:38 is the nucleic acid sequence of the coding sequence for INK101.

SEQ ID NO:39 is the amino acid sequence of peptide TBP101-DP as described in Example 5.

SEQ ID NOs:40 and 41 are the nucleic acid sequences of oligomers used in the site-directed mutagenesis of plasmid pINK101, as described in Example 5.

SEQ ID NO:42 is the nucleic acid sequence of plasmid pINK101-DP.

SEQ ID NO: 43 is the amino acid sequence of peptide IBT3.

SEQ ID NOs:44, 45, and 48-51 are the nucleic acid sequences of oligonucleotides used in site-directed mutagenesis, as described in Example 5.

SEQ ID NOs:46 and 47 are the nucleic acid sequences of primers used to amplify a fragment of the enzyme ketosteroid isomerase, as described in Example 5.

SEQ ID NO:52 is the amino acid sequence of a hair-binding peptide having a cysteine residue added to the C-terminus.

DETAILED DESCRIPTION OF THE INVENTION

The invention relates to a method for enhancing the effects of colorants, conditioners and other benefit agents using hair or skin-binding peptides as a sealant. The invention is useful because the method may be used to color or condition hair and skin, providing enhanced durability compared to traditional methods.

The following definitions are used herein and should be referred to for interpretation of the claims and the specification.

The term "invention" or "present invention" as used herein is a non-limiting term and is not intended to refer to any single embodiment of the particular invention but encompasses all possible embodiments as described in the specification and the claims.

"HBP" means hair-binding peptide.

"SBP" means skin-binding peptide.

"HCA" means hair conditioner.

"SCA" means skin conditioner.

"BA" means benefit agent.

The term "peptide" refers to two or more amino acids joined to each other by peptide bonds or modified peptide bonds.

The term "hair-binding peptide" refers to peptide sequences that bind with high affinity to hair. The hair-binding peptides of the invention are from about 7 amino acids to about 50 amino acids, more preferably, from about 7 amino acids to about 25 amino acids, most preferably from about 7 to about 20 amino acids in length.

The term "skin-binding peptide" refers to peptide sequences that bind with high affinity to skin. The skin-binding peptides of the invention are from about 7 amino acids to about 50 amino acids, more preferably, from about 7 amino acids to about 25 amino acids, most preferably from about 7 to about 20 amino acids in length.

The term "benefit agent" is a general term that refers to an agent that provides a cosmetic or prophylactic effect when applied to skin or hair. Benefit agents typically include conditioners, colorants, fragrances, whiteners, sunscreens, and the like along with other substances commonly used in the personal care industry.

The term "hair" as used herein refers to human hair, eyebrows, and eyelashes.

The term "skin" as used herein refers to human skin, or substitutes for human skin, such as pig skin, Vitro-Skin® and EpiDerm™. Skin as used herein as a body surface will generally comprise a layer of epithelial cells and may additionally comprise a layer of endothelial cells.

The terms "coupling" and "coupled" as used herein refer to any chemical association and include both covalent and non-covalent interactions.

The term "stringency" as it is applied to the selection of the hair-binding and skin-binding peptides of the present invention, refers to the concentration of the eluting agent (usually detergent) used to elute peptides from the hair or skin. Higher concentrations of the eluting agent provide more stringent conditions.

The term "peptide-hair complex" means structure comprising a peptide bound to a hair fiber via a binding site on the peptide.

The term "peptide-skin complex" means structure comprising a peptide bound to the skin via a binding site on the peptide.

The term "peptide-substrate complex" refers to either peptide-hair or peptide-skin complexes.

The term "nanoparticles" are herein defined as particles with an average particle diameter of between 1 and 500 nm. Preferably, the average particle diameter of the particles is between about 1 and 200 nm. As used herein, "particle size" and "particle diameter" have the same meaning. Nanoparticles include, but are not limited to, metallic, semiconductor, polymer, or other organic or inorganic particles.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

The term "phage" or "bacteriophage" refers to a virus that infects bacteria. Altered forms may be used for the purpose of the present invention. The preferred bacteriophage is derived from the "wild" phage, called M13. The M13 system can grow inside a bacterium, so that it does not destroy the cell it infects but causes it to make new phages continuously. It is a single-stranded DNA phage.

The term "phage display" refers to the display of functional foreign peptides or small proteins on the surface of bacteriophage or phagemid particles. Genetically engineered phage may be used to present peptides as segments of their native surface proteins. Peptide libraries may be produced by populations of phage with different gene sequences.

"PCR" or "polymerase chain reaction" is a technique used for the amplification of specific DNA segments (U.S. Pat. Nos. 4,683,195 and 4,800,159).

Standard recombinant DNA and molecular cloning techniques used herein are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-lnterscience (1987).

The invention provides a method for enhancing the effects of colorants, conditioners and other benefit agents using hair or skin-binding peptides as a sealant. The hair and skin-binding peptides have a binding affinity for hair or skin, respectively, and may be identified using combinatorial methods, such as phage display or may be empirically generated. Additionally, conjugates comprising a hair or skin-binding peptide coupled to a benefit agent may be used as the sealant. In the method of the invention, the peptide-based sealant may be applied either concomitantly with the application of the benefit agent, after the application of the benefit agent, or before the application of the benefit agent to seal the benefit agent to the hair or skin.

Identification of Hair-Binding and Skin-Binding Peptides

Hair-binding peptides (HBPs) and skin-binding peptides (SBPs) as defined herein are peptide sequences that specifically bind with high affinity to hair or skin, respectively. The hair or skin-binding peptides have no specific affinity for the benefit agent, but may interact nonspecifically with some benefit agents, particularly those that are polar. The hair-binding and skin-binding peptides of the invention are from about 7 amino acids to about 50 amino acids, more preferably, from about 7 amino acids to about 25 amino acids, most preferably from about 7 to about 20 amino acids in length. Suitable hair or skin-binding peptides may be selected using methods that are well known in the art or may be empirically generated.

The hair-binding or skin-binding peptides may be generated randomly and then selected against a specific hair or skin sample based upon their binding affinity for the substrate of interest, as described by Huang et al. in copending and commonly owned U.S. Patent Application Publication No. 2005/0050656, which is incorporated herein by reference. The generation of random libraries of peptides is well known and may be accomplished by a variety of techniques including, bacterial display (Kemp, D. J.; *Proc. Natl. Acad. Sci. USA* 78(7):4520-4524 (1981), and Helfman et al., *Proc. Natl. Acad. Sci.* USA 80(1):31-35, (1983)), yeast display (Chien et al., *Proc Natl Acad Sci* USA 88(21):9578-82 (1991)), combinatorial solid phase peptide synthesis (U.S. Pat. No. 5,449,754, U.S. Pat. No. 5,480,971, U.S. Pat. No. 5,585,275, U.S. Pat. No. 5,639,603), and phage display technology (U.S. Pat. No. 5,223,409, U.S. Pat. No. 5,403,484, U.S. Pat. No. 5,571,698, U.S. Pat. No. 5,837,500). Techniques to generate such biological peptide libraries are well known in the art. Exemplary methods are described in Dani, M., *J. of Receptor & Signal Transduction Res.*, 21 (4):447-468 (2001), Sidhu et al., *Methods in Enzymology* 328:333-363 (2000), Kay et al., *Combinatorial Chemistry & High Throughput Screening*, Vol. 8:545-551 (2005), and *Phage Display of Peptides and Proteins, A Laboratory Manual*, Brian K. Kay, Jill Winter, and John McCafferty, eds.; Academic Press, NY, 1996. Additionally, phage display libraries are available commercially from companies such as New England Biolabs (Beverly, Mass.).

A preferred method to randomly generate peptides is by phage display. Phage display is an in vitro selection technique in which a peptide or protein is genetically fused to a coat protein of a bacteriophage, resulting in display of fused peptide on the exterior of the phage virion, while the DNA encoding the fusion resides within the virion. This physical linkage between the displayed peptide and the DNA encoding it allows screening of vast numbers of variants of peptides, each linked to a corresponding DNA sequence, by a simple in vitro selection procedure called "biopanning". In its simplest form, biopanning is carried out by incubating the pool of phage-displayed variants with a target of interest that has been immobilized on a plate or bead, washing away unbound phage, and eluting specifically bound phage by disrupting the binding interactions between the phage and the target. The eluted phage is then amplified in vivo and the process is repeated, resulting in a stepwise enrichment of the phage pool in favor of the tightest binding sequences. After 3 or more rounds of selection/amplification, individual clones are characterized by DNA sequencing.

Specifically, the hair or skin-binding peptides may be selected using the following method. A suitable library of peptides is generated using the methods described above or the library is purchased from a commercial supplier. After the library of peptides has been generated, the library is then contacted with an appropriate amount of the test substrate, specifically a hair or skin sample. The library of peptides is dissolved in a suitable solution for contacting the sample. The test substrate may be suspended in the solution or may be immobilized on a plate or bead. A preferred solution is a buffered aqueous saline solution containing a surfactant. A suitable solution is Tris-buffered saline (TBS) with 0.5% Tween® 20. The solution may additionally be agitated by any means in order to increase the mass transfer rate of the peptides to the test substrate, thereby shortening the time required to attain maximum binding.

Upon contact, a number of the randomly generated peptides will bind to the test substrate to form a peptide-substrate complex (i.e., a peptide-hair or peptide-skin complex). Unbound peptide may be removed by washing. After all unbound material is removed, peptides having varying degrees of binding affinities for the test substrate may be fractionated by selected washings in buffers having varying stringencies. Increasing the stringency of the buffer used increases the required strength of the bond between the peptide and test substrate in the peptide-substrate complex.

A number of substances may be used to vary the stringency of the buffer solution in peptide selection including, but not limited to, acidic pH (1.5-3.0); basic pH (10-12.5); high salt concentrations such as $MgCl_2$ (3-5 M) and LiCl (5-10 M); water; ethylene glycol (25-50%); dioxane (5-20%); thiocyanate (1-5 M); guanidine (2-5 M); urea (2-8 M); and various concentrations of different surfactants such as SDS (sodium dodecyl sulfate), DOC (sodium deoxycholate), Nonidet P40, Triton X-100, Tween® 20, wherein Tween® 20 is preferred. These substances may be prepared in buffer solutions including, but not limited to, Tris-HCl, Tris-buffered saline, Tris-borate, Tris-acetic acid, triethylamine, phosphate buffer, and glycine-HCl, wherein Tris-buffered saline solution is preferred.

It will be appreciated that peptides having increasing binding affinities for the test substrate may be eluted by repeating the selection process using buffers with increasing stringencies. The eluted peptides can be identified and sequenced by any means known in the art.

In one embodiment, the following method for generating the hair-binding or skin-binding peptides of the present invention may be used. A library of combinatorially generated phage-peptides is contacted with the test substrate of interest, to form phage peptide-substrate complexes. The phage-peptide-substrate complex is separated from uncomplexed peptides and unbound substrate, and the bound phage-peptides from the phage-peptide-substrate complexes are eluted from the complex, preferably by acid treatment. Then, the eluted phage-peptides are identified and sequenced. To identify peptide sequences that bind to one substrate but not to another, for example peptides that bind to hair, but not to skin or peptides that bind to skin, but not to hair, a subtractive panning step may be added. Specifically, the library of combinatorially generated phage-peptides is first contacted with the non-target to remove phage-peptides that bind to it. Then, the non-binding phage-peptides are contacted with the desired substrate and the above process is followed. Alternatively, the library of combinatorially generated phage-peptides may be contacted with the non-target and the desired substrate simultaneously. Then, the phage-peptide-substrate complexes are separated from the phage-peptide-non-target complexes and the method described above is followed for the desired phage-peptide-hair or phage-peptide-skin complexes.

Alternatively, a modified phage display screening method for isolating peptides with a higher affinity for hair or skin may be used. In the modified method, the phage-peptide-substrate complexes are formed as described above. Then, these complexes are treated with an elution buffer. Any of the elution buffers described above may be used. Preferably, the elution buffer is an acidic solution. Then, the remaining, elution-resistant phage-peptide-substrate complexes are used to directly infect a bacterial host cell, such as *E. coli* ER2738. The infected host cells are grown in an appropriate growth medium, such as LB (Luria-Bertani) medium, and this culture is spread onto agar, containing a suitable growth medium, such as LB medium with IPTG (isopropyl β-D-thiogalactopyranoside) and S-Gal™. After growth, the plaques are picked for DNA isolation and sequencing to identify the peptide sequences with a high binding affinity for the substrate of interest. Alternatively, PCR may be used to identify the elution-resistant phage-peptides from the modified phage display screening method, described above, by directly carrying out PCR on the phage-peptide-substrate complexes using the appropriate primers, as described by Janssen et al. in U.S. Patent Application Publication No. 2003/0152976, which is incorporated herein by reference.

Shampoo-resistant hair-binding peptides may be selected using a modified biopanning method as described by O'Brien et al. in copending and commonly owned U.S. Patent Application Publication No. 2006/0073111, which is incorporated herein by reference. Similarly, hair conditioner-resistant hair-binding peptides and skin care composition resistant skin-binding peptides may be identified using the methods described by Wang et al. (copending and commonly owned U.S. patent application Ser. No. 11/359,163) and Wang et al. (copending and commonly owned U.S. patent application Ser. No. 11/359,162), respectively. In those methods, either the initial library of phage peptides is dissolved in the matrix of interest (i.e., a shampoo matrix, a hair conditioner matrix, or a skin care composition matrix) for contacting with the substrate, or the phage-peptide substrate complex, after it is formed by contacting the substrate with the library of phage peptides, as described above, is contacted with the matrix of interest. The biopanning method is then conducted as described above. The shampoo matrix, hair conditioner matrix, or skin care composition matrix may be a full strength commercial product or a dilution thereof.

Suitable hair-binding peptides and skin-binding peptides may be generated using the methods described herein. Additionally, any known hair-binding or skin-binding peptide may be used, such as those reported by Huang et al., (copending and commonly owned U.S. Patent Application Publication No. 2005/0050656, and U.S. Patent Application Publication No. 2005/0226839), Estell et al. (WO 0179479); Murray et al., (U.S. Patent Application Publication No. 2002/0098524); Janssen et al., (U.S. Patent Application Publication No. 2003/0152976); Janssen et al., (WO 04048399), O'Brien et al. (copending and commonly owned U.S. Patent Application Publication No. 2006/0073111), Wang et al. (copending and commonly owned U.S. patent application Ser. No. 11/359,163) and Wang et al. (copending and commonly owned U.S. patent application Ser. No. 11/359,162), all of which are incorporated herein by reference. Non-limiting examples of suitable hair-binding and skin-binding peptides are given in Table 1.

Alternatively, hair and skin-binding peptide sequences may be generated empirically by designing peptides that comprise positively charged amino acids, which can bind to hair and skin via electrostatic interaction, as described by Rothe et al. (WO 2004/000257). The empirically generated hair and skin-binding peptides have between about 7 amino acids to about 50 amino acids, and comprise at least about 40 mole % positively charged amino acids, such as lysine, arginine, and histidine. Peptide sequences containing tripeptide motifs such as HRK, RHK, HKR, RKH, KRH, KHR, HKX, KRX, RKX, HRX, KHX and RHX are most preferred where X can be any natural amino acid but is most preferably selected from neutral side chain amino acids such as glycine, alanine, proline, leucine, isoleucine, valine and phenylalanine. In addition, it should be understood that the peptide sequences must meet other functional requirements in the end use including solubility, viscosity and compatibility with other components in a formulated product and will therefore vary according to the needs of the application. In some cases the peptide may contain up to 60 mole % of amino acids not comprising histidine, lysine or arginine. Suitable empirically generated hair-binding and skin-binding peptides include, but are not limited to, SEQ ID NOs:8-12 (see Table 1).

It may also be beneficial to use a mixture of different hair-binding or skin-binding peptides. The peptides in the mixture need to be chosen so that there is no interaction between the peptides that mitigates the beneficial effect. Suitable mixtures of hair-binding or skin-binding peptides may be determined by one skilled in the art using routine experimentation. Additionally, it may be desirable to link two or more hair-binding peptides or skin-binding peptides together, either directly or through a spacer, to enhance the interaction of the peptide to the substrate. Methods to prepare the multiple peptide compositions and suitable spacers are described below. Non-limiting examples are given in Table 1.

TABLE 1

Examples of Hair-Binding and Skin-Binding Peptide Sequences

| Body Surface | SEQ ID NO: | Sequence |
|---|---|---|
| Hair (Shampoo Resistant) | 1 | TPPELLHGDPRS |
| Hair (Shampoo Resistant) | 2 | NTSQLST |
| Hair | 3 | RTNAADHP |
| Hair | 4 | RTNAADHPAAVT |
| Hair | 5 | IPWWNIRAPLNA |
| Hair | 6 | DLTLPFH |
| Hair and Skin (empirical) | 8 | KRGRHKRPKRHK |
| Hair and Skin (empirical) | 9 | RLLRLLR |
| Hair and Skin (empirical) | 10 | HKPRGGRKKALH |
| Hair and Skin (empirical) | 11 | KPRPPHGKKHRPKHRPKK |
| Hair and Skin (empirical) | 12 | RGRPKKGHGKRPGHRARK |
| Hair (Multi-copy) | 16 | PNTSQLSTGGGRTNAADHPKCGGG NTSQLSTGGGRTNAADHPKCGGG NTSQLSTGGGRTNAADHPKC |
| Hair (Multi-copy) | 17 | PRTNAADHPAAVTGGGCGGGRTNAAD HPAAVTGGGCGGGRTNAADHPAAVTG GGC |
| Hair (Multi-copy) | 18 | PRTNAADHPAAVTGGGCGGGIPWWNI RAPLNAGGGCGGGDLTLPFHGGGC |
| Hair (Multi-copy) | 19 | PRTNAADHPGGGTPPELLHGDPRSKC GGGRTNAADHPGGGTPPELLHGDPRS KCGGGRTNAADHPGGGTPPELLHGDP RSKC |
| Hair (Multi-copy) | 20 | PTPPTNVLMLATKGGGRTNAADHPKC GGGTPPTNVLMLATKGGGRTNAADHP KCGGGTPPTNVLMLATKGGGRTNAAD HPKC |
| Hair (Multi-copy) | 21 | PRTNAADHPGGGTPPTNVLMLATKKC GGGRTNAADHPGGGTPPTNVLMLATK KCGGGRTNAADHPGGGTPPTNVLMLA TKKC |
| Hair (with cysteine at C-terminus) | 52 | TPPELLHGDPRSC |
| Hair | 53 | EQISGSLVAAPW |
| Hair | 54 | TDMQAPTKSYSN |
| Hair | 55 | ALPRIANTWSPS |
| Hair | 56 | LDTSFPPVPFHA |
| Hair (Shampoo Resistant) | 57 | TPPTNVLMLATK |
| Hair (Conditioner Resistant) | 58 | STLHKYKSQDPTPHH |
| Hair (Shampoo and Conditioner Resistant) | 59 | GMPAMHWIHPFA |
| Hair (Shampoo and Conditioner Resistant) | 60 | HDHKNQKETHQRHAA |
| Hair (Shampoo and Conditioner Resistant) | 61 | HNHMQERYTDPQHSPSVNGL |
| Hair (Shampoo and Conditioner Resistant) | 62 | TAEIQSSKNPNPHPQRSWTN |
| Skin | 7 | TPFHSPENAPGS |
| Skin (Body Wash Resistant) | 63 | TMGFTAPRFPHY |
| Skin (Body Wash Resistant) | 64 | SVSVGMKPSPRP |
| Skin (Body Wash Resistant) | 65 | NLQHSVGTSPVW |
| Skin (Body Wash Resistant) | 66 | QLSYHAYPQANHHAP |
| Skin (Body Wash Resistant) | 67 | SGCHLVYDNGFCDH |
| Skin (Body Wash Resistant) | 68 | ASCPSASHADPCAH |

TABLE 1-continued

Examples of Hair-Binding and Skin-Binding Peptide Sequences

| Body Surface | SEQ ID NO: | Sequence |
| --- | --- | --- |
| Skin (Body Wash Resistant) | 69 | NLCDSARDSPRCKV |
| Skin (Body Wash Resistant) | 70 | NHSNWKTAADFL |
| Skin (Body Wash Resistant) | 71 | SDTISRLHVSMT |
| Skin (Body Wash Resistant) | 72 | SPYPSWSTPAGR |
| Skin (Body Wash Resistant) | 73 | DACSGNGHPNNCDR |
| Skin (Body Wash Resistant) | 74 | DWCDTIIPGRTCHG |

Production of Hair and Skin-Binding Peptides

The hair and skin-binding peptides of the present invention may be prepared using standard peptide synthesis methods, which are well known in the art (see for example Stewart et al., *Solid Phase Peptide Synthesis*, Pierce Chemical Co., Rockford, Ill., 1984; Bodanszky, *Principles of Peptide Synthesis*, Springer-Verlag, New York, 1984; and Pennington et al., *Peptide Synthesis Protocols*, Humana Press, Totowa, N.J., 1994). Additionally, many companies offer custom peptide synthesis services.

Alternatively, the peptides of the present invention may be prepared using recombinant DNA and molecular cloning techniques. Genes encoding the hair-binding or skin-binding peptides may be produced in heterologous host cells, particularly in the cells of microbial hosts, as described by Huang et al. (U.S. Patent Application Publication No. 2005/0050656), and as exemplified in Example 5 herein. The peptides when prepared by recombinant DNA and molecular cloning may further comprise a proline (P) residue at the N-terminus and optionally an aspartic acid (D) residue at the C-terminus. These additional residues result from the use of DP cleavage sites to separate the desired peptide sequence from peptide tags, used to promote inclusion body formation, and between tandem repeats of the peptide sequences.

Hair Benefit Agents

Any suitable hair benefit agent known in the art may be used in the method of the invention. The hair benefit agent has affinity to hair. As used herein, "having affinity to hair" means that the benefit agent adsorbs onto the surface of the hair or absorbs into the hair. Suitable hair benefit agents include, but are not limited to, hair colorants and hair conditioners.

Hair colorants, as herein defined, are any dye, pigment, nanoparticle, and the like that may be used to change the color of hair. Hair coloring agents are well known in the art (see for example Green et al., WO 0107009, incorporated herein by reference, CFTA *International Color Handbook*, 2$^{nd}$ ed., Micelle Press, England (1992) and *Cosmetic Handbook*, US Food and Drug Administration, FDA/IAS Booklet (1992)), and are available commercially from various sources (for example Bayer, Pittsburgh, Pa.; Ciba-Geigy, Tarrytown, N.Y.; ICI, Bridgewater, N.J.; Sandoz, Vienna, Austria; BASF, Mount Olive, N.J.; and Hoechst, Frankfurt, Germany). Suitable hair coloring agents include, but are not limited to, dyes, such 4-hydroxypropylamino-3-nitrophenol, 4-amino-3-nitrophenol, 2-amino-6-chloro-4-nitrophenol, 2-nitro-paraphenylenediamine, N,N-hydroxyethyl-2-nitro-phenylenediamine, 4-nitro-indole, 2-nitro-5-glyceryl methylaniline, 3-metylamino-4-nitrophenoxyethanol, 3-nitro-p-hydroxyethylaminophenol, hydroxyanthraquinoneaminopropylmethyl morpholinium methosulfate, Henna, HC Blue 1, HC Blue 2, HC Yellow 4, HC Red 3, HC Red 5, HC Red 7, HC Violet 1, HC Violet 2, HC Blue 7, HC Blue 10, HC Blue 12, HC Yellow 2, HC Yellow 6, HC Yellow 8, HC Yellow 12, HC Orange 2, HC Orange 3, HC Brown 2, D&C Yellow 1, D&C Yellow 3, D&C Blue 1, Disperse Blue 3, Disperse Violet 1, Disperse Orange, Disperse Violet 4, Disperse Black 9, Basic Orange 31, Basic Yellow 57, Basic Yellow 87, HC Yellow No. 9, Basic Blue 26, Basic Blue 7, Basic Blue 99, Basic Violet 14, Basic Violet 2, Basic Brown 16, Basic Brown 17, Basic Red 2, Basic Red 51, Acid Red 33, Brilliant Black 1, eosin derivatives such as D&C Red No. and halogenated fluorescein derivatives such as D&C Red No. 27, D&C Red Orange No. 5 in combination with D&C Red No. 21 and D&C Orange No. 10; and pigments, D&C Red No. 36, D&C Red No. 30, D&C Orange No. 17, Green 3 Lake, Ext. Yellow 7 Lake, Orange 4 Lake, and Red 28 Lake; the calcium lakes of D&C Red Nos. 7, 11, 31 and 34, the barium lake of D&C Red No. 12, the strontium lake D&C Red No. 13, the aluminum lakes of FD&C Yellow No. 5, of FD&C Yellow No. 6, of FD&C No. 40, of D&C Red Nos. 21, 22, 27, and 28, of FD&C Blue No. 1, of D&C Orange No. 5, of D&C Yellow No. 10, the zirconium lake of D&C Red No. 33; Cromophthal® Yellow 131AK (Ciba Specialty Chemicals), Sunfast® Magenta 122 (Sun Chemical) and Sunfast® Blue 15:3 (Sun Chemical), iron oxides, calcium carbonate, aluminum hydroxide, calcium sulfate, kaolin, ferric ammonium ferrocyanide, magnesium carbonate, carmine, barium sulfate, mica, bismuth oxychloride, zinc stearate, manganese violet, chromium oxide, titanium dioxide, titanium dioxide nanoparticles, zinc oxide, barium oxide, ultramarine blue, bismuth citrate, and white minerals such as hydroxyapatite, and Zircon (zirconium silicate), and carbon black particles.

Metallic and semiconductor nanoparticles may also be used as hair coloring agents due to their strong emission of light (Vic et al., U.S. Patent Application Publication No. 2004/0010864). The metallic nanoparticles include, but are not limited to, particles of gold, silver, platinum, palladium, iridium, rhodium, osmium, iron, copper, cobalt, and alloys composed of these metals. An "alloy" is herein defined as a homogeneous mixture of two or more metals. The "semiconductor nanoparticles" include, but are not limited to, particles of cadmium selenide, cadmium sulfide, silver sulfide, cadmium sulfide, zinc oxide, zinc sulfide, zinc selenide, lead sulfide, gallium arsenide, silicon, tin oxide, iron oxide, and indium phosphide. The nanoparticles are stabilized and made water-soluble by the use of a suitable organic coating or monolayer. As used herein, monolayer-protected nanoparticles are one type of stabilized nanoparticle. Methods for the preparation of stabilized, water-soluble metal and semiconductor nanoparticles are known in the art, and suitable examples are described by Huang et al. in copending and commonly owned U.S. Patent Application Publication No. 2004/0115345, which is incorporated herein by reference. The color of the nanoparticles depends on the size of the particles. Therefore, by controlling the size of the nanoparticles, different colors may be obtained.

Additionally, organic and inorganic nanoparticles, having an attached, adsorbed, or absorbed dye, may be used as a hair coloring agent. For example, the hair coloring agent may be colored polymer nanoparticles. Exemplary polymer nanoparticles include, but are not limited to, microspheres comprised of materials such as polystyrene, polymethylmethacrylate, polyvinyltoluene, styrene/butadiene copolymer, and latex. For use in the invention, the colored microspheres have a diameter of about 10 nanometers to about 2 microns. The microspheres may be colored by coupling any suitable dye, such as those described above, to the microspheres. The dyes may be coupled to the surface of the microsphere or adsorbed within the porous structure of a porous microsphere. Suitable microspheres, including undyed and dyed microspheres that are functionalized to enable covalent attachment, are available from companies such as Bang Laboratories (Fishers, Ind.).

Hair conditioners as herein defined are agents which improve the appearance, texture, and sheen of hair as well as increasing hair body or suppleness. Hair conditioners, include, but are not limited to, styling aids, hair straightening aids, hair strengthening aids, and volumizing agents, such as nanoparticles. Hair conditioners are well known in the art, see for example Green et al., supra, and are available commercially from various sources. Suitable examples of hair conditioners include, but are not limited to, cationic polymers, such as cationized guar gum, diallyl quaternary ammonium salt/acrylamide copolymers, quaternized polyvinylpyrrolidone and derivatives thereof, and various polyquaternium-compounds; long chain alkyl groups (i.e., $C_8$ to $C_{24}$); cationic surfactants, such as stearalkonium chloride, centrimonium chloride, and Sapamin hydrochloride; fatty alcohols, such as behenyl alcohol; fatty amines, such as stearyl amine; waxes; esters; nonionic polymers, such as polyvinylpyrrolidone, polyvinyl alcohol, and polyethylene glycol; silicones; siloxanes, such as decamethylcyclopentasiloxane; polymer emulsions, such as amodimethicone; and nanoparticles, such as silica nanoparticles and polymer nanoparticles. The preferred hair conditioners of the present invention contain amine or hydroxyl functional groups to facilitate coupling to the hair-binding peptides, as described below. Examples of preferred conditioners are octylamine (CAS No. 111-86-4), stearyl amine (CAS No. 124-30-1), behenyl alcohol (CAS No. 661-19-8, Cognis Corp., Cincinnati, Ohio), vinyl group terminated siloxanes, vinyl group terminated silicone (CAS No. 68083-19-2), vinyl group terminated methyl vinyl siloxanes, vinyl group terminated methyl vinyl silicone (CAS No. 68951-99-5), hydroxyl terminated siloxanes, hydroxyl terminated silicone (CAS No. 80801-30-5), amino-modified silicone derivatives, [(aminoethyl)amino]propyl hydroxyl dimethyl siloxanes, [(aminoethyl)amino]propyl hydroxyl dimethyl silicones, and alpha-tridecyl-omega-hydroxy-poly(oxy-1,2-ethanediyl) (CAS No. 24938-91-8).

Skin Benefit Agents

Any suitable skin benefit agent known in the art may be used in the method of the invention. The skin benefit agent has affinity to skin. As used herein, having "affinity to skin" means that the benefit agent is adsorbed onto the surface of the skin. Suitable skin benefit agents include, but are not limited to, skin colorants, skin conditioners, and sunscreens.

Skin colorants, as herein defined, are any dye, pigment, nanoparticle, and the like that may be used to change the color of skin. Any of the dyes, pigments, or nanoparticles described above may be used as a skin colorant. The coloring agent may also be a sunless tanning agent, such as dihydroxyacetone, that produces a tanned appearance on the skin without exposure to the sun.

Skin conditioners as herein defined include, but are not limited to, astringents, which tighten skin; exfoliants, which remove dead skin cells; emollients, which help maintain a smooth, soft, pliable appearance; humectants, which increase the water content of the top layer of skin; occlusives, which retard evaporation of water from the skin's surface; and miscellaneous compounds that enhance the appearance of dry or damaged skin or reduce flaking and restore suppleness. Any suitable known skin conditioner may be used in the method of the invention. Skin conditioners are well known in the art, see for example Green et al., supra, and are available commercially from various sources. Suitable examples of skin conditioners include, but are not limited to, alpha-hydroxy acids, beta-hydroxy acids, polyols, hyaluronic acid, D,L-panthenol, polysalicylates, vitamin A palmitate, vitamin E acetate, glycerin, sorbitol, silicones, silicone derivatives, lanolin, natural oils and triglyceride esters. The preferred skin conditioners of the present invention are polysalicylates, propylene glycol (CAS No. 57-55-6, Dow Chemical, Midland, Mich.), glycerin (CAS No. 56-81-5, Proctor & Gamble Co., Cincinnati, Ohio), glycolic acid (CAS No. 79-14-1, DuPont Co., Wilmington, Del.), lactic acid (CAS No. 50-21-5, Alfa Aesar, Ward Hill, Mass.), malic acid (CAS No. 617-48-1, Alfa Aesar), citric acid (CAS No. 77-92-9, Alfa Aesar), tartaric acid (CAS NO. 133-37-9, Alfa Aesar), glucaric acid (CAS No. 87-73-0), galactaric acid (CAS No. 526-99-8), 3-hydroxyvaleric acid (CAS No. 10237-77-1), salicylic acid (CAS No. 69-72-7, Alfa Aesar), and 1,3 propanediol (CAS No. 504-63-2, DuPont Co., Wilmington, Del.). Polysalicylates may be prepared by the method described by White et al. in U.S. Pat. No. 4,855,483, incorporated herein by reference. Glucaric acid may be synthesized using the method described by Merbouh et al. (*Carbohydr. Res.* 336:75-78 (2001). The 3-hydroxyvaleric acid may be prepared as described by Bramucci et al. in WO 02012530.

Sunscreens are substances that absorb, reflect, or scatter ultraviolet light at wavelengths from 290 to 400 nanometers. The sunscreens used in the invention may either be organic sunscreens or inorganic sunscreens. Organic sunscreens are herein defined as organic chemicals that absorb ultraviolet light of wavelengths between 290 and 400 nm. Organic sunscreens are well known in the art (see for example, Woddin et al., U.S. Pat. No. 5,219,558, which is incorporated herein by reference, in particular column 3 line 35 to column 4 line 23). Suitable examples include, but are not limited to, para-aminobenzoic acid (PABA), ethyl para-aminobenzoate, amyl para-aminobenzoate, octyl para-aminobenzoate, ethylhexyl dimethyl para-aminobenzoate (Padimate O), ethylene glycol salicylate, phenyl salicylate, octyl salicylate, benzyl salicylate, butylphenyl salicylate, homomenthyl salicylate (Homosalate), ethylhexyl salicylate (Octisalate), TEA-salicylate (Trolamine salicylate), benzyl cinnamate, 2-ethoxyethyl para-methoxycinnamate (such as Parsol® available from Givaudan-Roure Co.), ethylhexyl methoxycinnamate (Octinoxate), octyl para-methoxycinnamate, glyceryl mono(2-ethylhexanoate) dipara-methoxycinnamate, isopropyl para-methoxycinnamate, urocanic acid, ethyl urocanate, hydroxymethoxybenzophenone (Benzophenone-3), hydroxymethoxybenzophenonesulfonic acid (Benzophenone-4) and salts thereof, dihydroxymethoxybenzophenone (Benzophenone-8), sodium dihydroxymethoxybenzophenonedisulfonate, dihydroxybenzophenone, tetrahydroxybenzophenone, 4-tert-butyl-4'-methoxydibenzoylmethane (Avobenzone), phenylbenzimidazole sulfonic acid (Ensulizole), 2,4,6-trianilino-p-(carbo-2'-ethylhexyl-1'-oxy)-1,3,5-triazine, Octocrylene, menthyl anthranilate (Meradimate), and 2-(2-hydroxy-5-methylphenyl)benzotriazole.

Inorganic UV sunscreen materials are typically inorganic pigments and metal oxides including, but not limited to, titanium dioxide (such as SunSmart available from Cognis Co.), zinc oxide, and iron oxide. A preferred sunscreen is titanium dioxide nanoparticles. Suitable titanium dioxide nanoparticles are described in U.S. Pat. Nos. 5,451,390; 5,672,330; and 5,762,914. Titanium dioxide P25 is an example of a suitable commercial product available from Degussa (Parsippany, N.J.). Other commercial suppliers of titanium dioxide nanoparticles include Kemira (Helsinki, Finland), Sachtleben (Duisburg, Germany) and Tayca (Osaka, Japan).

The titanium dioxide nanoparticles typically have an average particle size diameter of less than 100 nanometers (nm) as determined by dynamic light scattering which measures the particle size distribution of particles in liquid suspension. The particles are typically agglomerates which may range from about 3 nm to about 6000 nm. Any process known in the art can be used to prepare such particles. The process may involve vapor phase oxidation of titanium halides or solution precipitation from soluble titanium complexes, provided that titanium dioxide nanoparticles are produced.

A preferred process to prepare titanium dioxide nanoparticles is by injecting oxygen and titanium halide, preferably titanium tetrachloride, into a high-temperature reaction zone, typically ranging from 400 to 2000 degrees centigrade. Under the high temperature conditions present in the reaction zone, nanoparticles of titanium dioxide are formed having high surface area and a narrow size distribution. The energy source in the reactor may be any heating source such as a plasma torch.

Conjugates Comprising a Hair or Skin-Binding Peptide Coupled to a Benefit Agent

In another embodiment, a conjugate comprising a hair or skin-binding peptide coupled to a benefit agent is used as the peptide-based sealant of the invention. The coupling interaction may be a covalent bond or a non-covalent interaction, such as hydrogen bonding, electrostatic interaction, hydrophobic interaction, or Van der Waals interaction. In the case of a non-covalent interaction, the peptide-based conjugate may be prepared by mixing the peptide with the benefit agent and an optional spacer and allowing sufficient time for the interaction to occur. The unbound materials may be separated from the resulting peptide-based conjugate using methods known in the art, for example, chromatographic methods.

The peptide-based conjugates may also be prepared by covalently attaching a specific hair-binding peptide or a skin-binding peptide to a benefit agent, either directly or through a spacer, as described by Huang et al. in U.S. Patent Application Publication No. 2005/0050656. The covalent coupling of inorganic sunscreens and organic sunscreens to a skin-binding peptide is described by Buseman-Williams, supra, and Lowe et al., supra, respectively.

Any known peptide or protein conjugation chemistry may be used to form the peptide-based conjugates used in the invention. Conjugation chemistries are well known in the art (see for example, Hermanson, *Bioconjugate Techniques*, Academic Press, New York (1996)). Suitable coupling agents include, but are not limited to, carbodiimide coupling agents, acid chlorides, isocyanates, epoxides, maleimides, and other functional coupling reagents that are reactive toward terminal amine and/or carboxylic acid groups, and sulfhydryl groups on the peptides. Additionally, it may be necessary to protect reactive amine or carboxylic acid groups on the peptide to produce the desired structure for the peptide-based sealant. The use of protecting groups for amino acids, such as t-butyloxycarbonyl (t-Boc), are well known in the art (see for example Stewart et al., supra; Bodanszky, supra; and Pennington et al., supra). In some cases it may be necessary to introduce reactive groups, such as carboxylic acid, alcohol, amine, isocyanate, or aldehyde groups on the benefit agent for coupling to the hair-binding or skin-binding peptide. These modifications may be done using routine chemistry such as oxidation, reduction, phosgenation, and the like, which is well known in the art.

It may also be desirable to couple the hair-binding peptide or skin-binding peptide to the benefit agent via a spacer. The spacer serves to separate the benefit agent from the peptide to ensure that the agent does not interfere with the binding of the peptide to the hair or skin. The spacer may be any of a variety of molecules, such as alkyl chains, phenyl compounds, ethylene glycol, amides, esters and the like. The spacer may be covalently attached to the peptide and the benefit agent using any of the coupling chemistries described above. In order to facilitate incorporation of the spacer, a bifunctional cross-linking agent that contains a spacer and reactive groups at both ends for coupling to the peptide and the benefit agent may be used.

Additionally, the spacer may be a peptide comprising any amino acid and mixtures thereof. The preferred peptide spacers are comprised of the amino acids proline, lysine, glycine, alanine, and serine, and mixtures thereof. In addition, the peptide spacer may contain a specific enzyme cleavage site, such as the protease Caspase 3 site which allows for the enzymatic removal of the benefit agent from the hair. The peptide spacer may be from 1 to about 50 amino acids, preferably from 1 to about 20 amino acids in length. Exemplary peptide spacers include, but are not limited, to SEQ ID NOs: 13-15. These peptide spacers may be linked to the binding peptide sequence by any method known in the art. For example, the entire binding peptide-peptide spacer diblock may be prepared using the standard peptide synthesis methods described supra. In addition, the binding peptide and peptide spacer blocks may be combined using carbodiimide coupling agents (see for example, Hermanson, *Bioconjugate Techniques*, Academic Press, New York (1996)), diacid chlorides, diisocyanates and other difunctional coupling reagents that are reactive to terminal amine and/or carboxylic acid groups on the peptides. Alternatively, the entire binding peptide-peptide spacer diblock may be prepared using the recombinant DNA and molecular cloning techniques described supra. The spacer may also be a combination of a peptide spacer and an organic spacer molecule, which may be prepared using the methods described above.

It may also be desirable to have multiple hair-binding or skin-binding peptides coupled to the benefit agent to enhance the interaction between the peptide-based benefit agent and the hair or skin, as described by Huang et al. (U.S. Patent Application Publication No. 2005/0050656). Either multiple copies of the same hair-binding or skin-binding peptide or a combination of different hair-binding or skin-binding peptides may be used. The multi-copy hair and skin-binding peptide may comprise various spacers as described above. Exemplary multi-copy hair-binding peptides include, but are not limited to, SEQ ID NOs:16-21.

Compositions Comprising a Hair-Binding Peptide

The hair-binding peptide may be applied to the hair from various compositions. For example, the hair-binding peptide may be applied to the hair from an aqueous solution comprising the hair-binding peptide. Alternatively, the hair-binding peptide may be applied to the hair from a hair care composition. Hair care compositions are herein defined as compositions for the treatment of hair including, but not limited to, shampoos, conditioners, rinses, lotions, aerosols, gels, mousses, and hair dyes. The hair-binding peptide is used in the composition at a concentration of about 0.01% to about 10%, preferably about 0.01% to about 5% by weight relative to the total weight of the composition. This proportion may vary as a function of the type of hair care composition. Additionally, the composition comprising a hair-binding peptide may further comprise a hair benefit agent. If the composition comprises a hair benefit agent, the benefit agent may be coupled to a hair-binding peptide, as described above. The concentration of the peptide in relation to the concentration of the benefit agent may need to be optimized for best results. Suitable hair-binding peptides, including multi-copy hair-binding peptides, are described above. Additionally, a mixture of different hair-binding peptides may be used in the composition. The hair-binding peptides in the mixture need to be chosen so that there is no interaction between the peptides that mitigates the beneficial effect. Suitable mixtures of hair-binding peptides may be determined by one skilled in the art using routine experimentation. If a mixture of hair-binding peptides is used in the composition, the total concentration of the peptides is about 0.01% to about 10% by weight relative to the total weight of the composition.

In another embodiment, the hair-binding peptide may be present in the composition as a conjugate comprising a hair-binding peptide coupled to a hair benefit agent, as described above. For example, the benefit agent may be a hair dye and the conjugate may comprise a hair-binding peptide coupled to a hair conditioner. Additionally, the benefit agent may be a hair dye and the conjugate may comprise a hair-binding peptide coupled to either the same hair dye or to another hair colorant. All these and other possible combinations are within the scope of the invention.

The composition comprising a hair-binding peptide may further comprise a cosmetically acceptable medium for hair care compositions, examples of which are described for example by Philippe et al. in U.S. Pat. No. 6,280,747, and by Omura et al. in U.S. Pat. No. 6,139,851 and Cannell et al. in U.S. Pat. No. 6,013,250, all of which are incorporated herein by reference. For example, these hair care compositions can be aqueous, alcoholic or aqueous-alcoholic solutions, the alcohol preferably being ethanol or isopropanol, in a proportion of from about 1 to about 75% by weight relative to the total weight, for the aqueous-alcoholic solutions. Additionally, the hair care compositions may contain one or more conventional cosmetic or dermatological additives or adjuvants including, but not limited to, antioxidants, preserving agents, fillers, surfactants, UVA and/or UVB sunscreens, fragrances, thickeners, wetting agents and anionic, nonionic or amphoteric polymers, and dyes or pigments.

Compositions Comprising a Skin-Binding Peptide

The skin-binding peptide may be applied to the skin from various compositions. For example, the skin-binding peptide may be applied to the skin from an aqueous solution comprising the skin-binding peptide. Alternatively, the skin-binding peptide is applied to the skin from a skin care composition. Skin care compositions are herein defined as compositions for the treatment of skin including, but not limited to, skin care, skin cleansing, make-up, and anti-wrinkle products. The skin-binding peptide is used in the composition at a concentration of about 0.01% to about 10%, preferably about 0.01% to about 5% by weight relative to the total weight of the composition. This proportion may vary as a function of the type of skin care composition. Additionally, the composition comprising a skin-binding peptide may further comprise a skin benefit agent. If the composition comprises a skin benefit agent, the benefit agent may be coupled to a skin-binding peptide, as described above. The concentration of the skin-binding peptide in relation to the concentration of the benefit agent may need to be optimized for best results. Suitable skin-binding peptides, including multi-copy skin-binding peptides, are described above. Additionally, a mixture of different skin-binding peptides may be used in the composition. The skin-binding peptides in the mixture need to be chosen so that there is no interaction between the peptides that mitigates the beneficial effect. Suitable mixtures of skin-binding peptides may be determined by one skilled in the art using routine experimentation. If a mixture of skin-binding peptides is used in the composition, the total concentration of the peptides is about 0.01% to about 10% by weight relative to the total weight of the composition.

In another embodiment, the skin-binding peptide may be present in the composition as a conjugate comprising a skin-binding peptide coupled to a skin benefit agent, as described above. For example, the benefit agent may be a skin conditioner and the conjugate may comprise a skin-binding peptide coupled to either the same or a different skin conditioner. The benefit agent may be a skin colorant and the conjugate may comprise a skin-binding peptide coupled to a skin conditioner. Additionally, the benefit agent may be a skin conditioner and the conjugate may comprise a skin-binding peptide coupled to a sunscreen. All these and other possible combinations are within the scope of the invention.

The composition comprising a skin-binding peptide may further comprise a cosmetically acceptable medium for skin care compositions, examples of which are described for example by Philippe et al. supra. For example, the cosmetically acceptable medium may be an anhydrous composition containing a fatty substance in a proportion generally of from about 10 to about 90% by weight relative to the total weight of the composition, where the fatty phase contains at least one liquid, solid or semi-solid fatty substance. The fatty substance includes, but is not limited to, oils, waxes, gums, and so-called pasty fatty substances. Alternatively, the compositions may be in the form of a stable dispersion such as a water-in-oil or oil-in-water emulsion. Additionally, the compositions may contain one or more conventional cosmetic or dermatological additives or adjuvants including, but not limited to, antioxidants, preserving agents, fillers, surfactants, UVA and/or UVB sunscreens, fragrances, thickeners, wetting agents and anionic, nonionic or amphoteric polymers, and dyes or pigments.

Methods for Applying a Benefit Agent to Hair

The peptide-based sealants of the invention are used to enhance the durability of common hair benefit agents, for example, colorants or conditioners. The hair benefit agent may be applied to the hair from any suitable composition. The hair benefit agent may be present in the composition in the form of a conjugate with a hair-binding peptide, as described above. In one embodiment, the hair benefit agent is applied to the hair from a conventional hair care composition, for example a temporary hair dye or hair conditioner. These hair care compositions are well known in the art and suitable compositions are described above.

In one embodiment the hair benefit agent is applied to the hair for a time sufficient for the hair benefit agent to bind to the hair, typically between about 5 seconds to about 60 minutes. Optionally, the hair may be rinsed to remove the benefit agent that has not bound to the hair. Then, a composition comprising a hair-binding peptide is applied to the hair for a time sufficient for the hair-binding peptide to bind to the hair, typically between about 5 seconds to about 60 minutes. The composition comprising the hair-binding peptide may be rinsed from the hair or left on the hair.

In another embodiment, the composition comprising a hair-binding peptide is applied to the hair for a time sufficient for the hair-binding peptide to bind to the hair, typically between about 5 seconds to about 60 minutes. Optionally, the hair may be rinsed to remove the hair-binding peptide composition that has not bound to the hair. Then, a hair benefit agent is applied to the hair for a time sufficient for the benefit agent to bind to the hair, typically between about 5 seconds to about 60 minutes. The unbound hair benefit agent may be rinsed from the hair or left on the hair.

In another embodiment, the hair benefit agent and the composition comprising a hair-binding peptide are applied to the hair concomitantly for a time sufficient for the benefit agent and the hair-binding peptide to bind to hair, typically between about 5 seconds to about 60 minutes. Optionally, the hair may be rinsed to remove the unbound benefit agent and the composition comprising a hair-binding peptide from the hair.

In another embodiment, the hair benefit agent is provided as part of the composition comprising a hair-binding peptide. In that embodiment, the composition comprising the hair benefit agent and the hair-binding peptide is applied to the hair for a time sufficient for the hair benefit agent and the hair-binding peptide to bind to hair, typically between about 5 seconds to about 60 minutes. The composition comprising the hair benefit agent and the hair-binding peptide may be rinsed from the hair or left on the hair.

In any of the methods described above, the composition comprising a hair-binding peptide may optionally be reapplied to the hair after the application of the hair benefit agent and the composition comprising a hair-binding peptide in order to further enhance the durability of the benefit agent.

Additionally, in any of the methods described above, a composition comprising a polymeric sealant may optionally be applied to the hair after the application of the hair benefit agent and the composition comprising a hair-binding peptide in order to further enhance the durability of the benefit agent. The composition comprising the polymeric sealant may be an aqueous solution or a hair care composition comprising the polymeric sealant. Typically, the polymeric sealant is present in the composition at a concentration of about 0.25% to about 10% by weight based on the total weight of the composition. Polymeric sealants are well know in the art of personal care products and include, but are not limited to, poly(allylamine), acrylates, acrylate copolymers, polyurethanes, carbomers, methicones, amodimethicones, polyethylenene glycol, beeswax, siloxanes, and the like. The choice of polymeric sealant depends on the particular benefit agent and the hair-binding peptide used. The optimum polymeric sealant may be readily determined by one skilled in the art using routine experimentation.

Method for Applying a Benefit Agent to Skin

The peptide-based sealants of the invention are used to enhance the durability of common skin benefit agents, for example, colorants, conditioners, sun screens, fragrances, and the like. The skin benefit agent may be applied to the skin from any suitable composition. The skin benefit agent may be present in the composition in the form of a conjugate with a skin-binding peptide, as described above. In one embodiment, the benefit agent may be applied to the skin from a conventional skin care composition, for example a skin colorant, skin conditioner, sunscreen, and the like, which is well known in the art.

In one embodiment, the skin benefit agent is applied to the skin for a time sufficient for the skin benefit agent to bind to the skin, typically between about 5 seconds to about 60 minutes. Optionally, the skin may be rinsed to remove the benefit agent that has not bound to skin. Then, a composition comprising a skin-binding peptide is applied to the skin for a time sufficient for the skin-binding peptide agent to bind to the skin, typically between about 5 seconds to about 60 minutes. The composition comprising the skin-binding peptide may be rinsed from the skin or left on the skin.

In another embodiment, the composition comprising a skin-binding peptide is applied to the skin for a time sufficient for the skin-binding peptide to bind to the skin, typically between about 5 seconds to about 60 minutes. Optionally, the skin may be rinsed to remove the skin-binding peptide composition that has not bound to the skin. Then, a skin benefit agent is applied to the skin for a time sufficient for the benefit agent to bind to the skin, typically between about 5 seconds to about 60 minutes. The unbound skin benefit agent may be rinsed from the skin or left on the skin.

In another embodiment, the skin benefit agent and the composition comprising a skin-binding peptide are applied to the skin concomitantly for a time sufficient for the benefit agent and the skin-binding peptide to bind to skin, typically between about 5 seconds to about 60 minutes. Optionally, the skin may be rinsed to remove the unbound benefit agent and the composition comprising a skin-binding peptide from the skin.

In another embodiment, the skin benefit agent is provided as part of the composition comprising a skin-binding peptide. In that embodiment, the composition comprising the skin benefit agent and the skin-binding peptide is applied to the skin for a time sufficient for the skin benefit agent and the skin-binding peptide to bind to the skin, typically between about 5 seconds to about 60 minutes. The composition comprising the skin benefit agent and the skin-binding peptide may be rinsed from the skin or left on the skin.

In any of the methods described above, the composition comprising a skin-binding peptide may optionally be reapplied to the skin after the application of the skin benefit agent and the composition comprising a skin-binding peptide in order to further enhance the durability of the benefit agent.

Additionally, in any of the methods described above, a composition comprising a polymeric sealant may optionally be applied to the skin after the application of the skin benefit agent and the composition comprising a skin-binding peptide in order to further enhance the durability of the benefit agent. The composition comprising the polymeric sealant may be an aqueous solution or a skin care composition comprising the polymeric sealant. Typically, the polymeric sealant is present in the composition at a concentration of about 0.25% to about 10% by weight based on the total weight of the composition. Polymeric sealants are well know in the art of personal care products and include, but are not limited to, poly(allylamine), acrylates, acrylate copolymers, polyurethanes, carbomers, methicones, amodimethicones, polyethylenene glycol, beeswax, siloxanes, and the like. The choice of polymeric sealant depends on the particular benefit agent and the skin-binding peptide used. The optimum polymeric sealant may be readily determined by one skilled in the art using routine experimentation.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "sec" means second(s), "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "M" means molar, "mol" means mole(s), mmol" means millimole(s), "µmol" means micromole(s), "pmol" means picomole(s), "g" means gram(s), "µg" means microgram(s), "mg" means milligram(s), "wt %" means percent by weight, "vol %" means percent by volume, "MALDI" means matrix assisted, laser desorption ionization, "$OD_{600}$" means the optical density measured at a wavelength of 600 nm, "rpm" means revolutions per minute, "atm" means atmosphere(s), "kPa" means kilopascals, "SLPM" means standard liter per minute, "psi" means pounds per square inch, "RCF" means relative centrifugal field.

Example 1

Coloring Hair Using a Combinatorially Generated Hair-binding Peptide as Sealant The purpose of this Example was to demonstrate the coloring of hair using a hair dye in combination with a hair-binding peptide as a sealant. The hair-binding peptide used in this Example was identified using phage display screening by Huang et al. (U.S. Patent Application Publication No. 2005/0050656).

The hair-binding peptide IB5 with a cysteine residue added to the C-terminus, given as SEQ ID NO:52, was obtained from SynPep (Dublin, Calif.). This peptide (25 mg) was added to 10 g of a 1 wt % stock solution of Basic Violet #2 (Aldrich, Milwaukee, Wis.; CAS 3248-91-7) in water and the solution was allowed to stir overnight. A natural white hair swatch (International Hair Importers & Products Inc., Bellerose, N.Y.) was inserted into a 13 mm×100 mm test tube and 8 mL of the peptide/dye mixture was injected into the test tube. The hair swatch was stirred in contact with the colorant solution for 30 min using a magnetic stirrer; then was removed and air dried for 30 min.

The hair swatch was then subjected to a water rinse using copious amounts of deionized water, followed by five shampoo treatments over a period of several days. The shampoo treatment involved the application of a commercially available shampoo, Pantene Pro-V Sheer Volume (Proctor & Gamble, Cincinnati, Ohio), to the hair as follows. A quarter-sized drop of the shampoo was distributed evenly over the hair swatch and then was massaged aggressively into the hair for 30 sec, after which the hair swatch was rinsed with water to remove the shampoo. The hair swatch was then dried at room temperature.

The procedure described above was repeated without the addition of the hair-binding peptide sealant to serve as a control. Color durability was rated qualitatively using visual observation of color retention against the control using the following scale:

"Same": indicates the same amount of color loss as the control;
"Fair": indicates a small improvement in color retention compared to the control;
"Good": indicates a large improvement in color retention compared to the control; and
"Very Good": indicates minimal color loss.

After the shampoo treatment, the color of the hair swatch treated with the dye and the hair-binding peptide sealant was evaluated to be "very good" indicating that there was minimal colorant loss after shampoo treatment. The control without the hair-binding peptide showed significant color loss after the shampoo treatment. These results demonstrate the effectiveness of the hair-binding peptide as a sealant for hair dyes.

This experiment was repeated using a stock solution of Basic Violet #2 having a concentration of 0.75 wt % or 0.50 wt % in place of the 1.0 wt % concentration described above. With the 0.75 wt % dye concentration the color of the hair swatch treated with the dye and the hair-binding peptide sealant was evaluated to be "fair" indicating that there was a small improvement in color retention compared to the control. When the 0.50 wt % dye concentration was used, the color of the hair swatch treated with the dye and the hair-binding peptide sealant was evaluated to be "same" indicating that the color loss was the same as the control. These results demonstrate that the concentration of the dye and the ratio of the dye to the hair-binding peptide need to be optimized for best results.

Example 2

Coloring Hair Using an Empirically Generated Hair-Binding Peptide as Sealant The purpose of this Example was to demonstrate the coloring of hair using a hair dye in combination with a hair-binding peptide as a sealant. The hair-binding peptide used in this Example was generated empirically.

The empirically generated hair-binding peptide, given as SEQ ID NO:8, was obtained from SynPep (Dublin, Calif.). This peptide (27 mg) was added to 10 g of a 0.5 wt % stock solution of Basic Violet #2 (Aldrich, Milwaukee, Wis.; CAS 3248-91-7) in water and the solution was allowed to stir overnight. A natural white hair swatch (International Hair Importers & Products Inc., Bellerose, N.Y.) was inserted into a 13 mm×100 mm test tube and 8 mL of the peptide/dye mixture was injected into the test tube. The hair swatch was stirred in contact with the colorant solution for 30 min using a magnetic stirrer; then was removed and air dried for 30 min.

The hair swatch was then subjected to a water rinse using copious amounts of deionized water, followed by eight shampoo treatments over a period of several days. The shampoo treatment involved the application of a commercially available shampoo, Pantene Pro-V Sheer Volume (Proctor & Gamble, Cincinnati, Ohio), to the hair as follows. A quarter-sized drop of the shampoo was distributed evenly over the hair swatch and then was massaged aggressively into the hair for 30 sec, after which the hair swatch was rinsed with water to remove the shampoo. The hair swatch was then dried at room temperature.

The procedure described above was repeated without the addition of the hair-binding peptide sealant to serve as a control. Color durability was rated qualitatively using visual observation of color retention against the control using the scale described in Example 1.

After the shampoo treatment, the color of the hair swatch treated with the dye and the hair-binding peptide sealant was evaluated to be "fair" indicating that there was a small improvement in color retention compared to the control.

Example 3

Coloring Hair Using a Conjugate Comprising a Hair-Binding Peptide Coupled to a Hair Conditioner as Sealant The purpose of this Example was to demonstrate the coloring of hair using a hair dye in combination with a conjugate comprising a hair-binding peptide covalently bound to a hair conditioner as a sealant.

Preparation of Octadecyl-Hair-Binding Peptide Conjugate:

Octadecylisocyanate (70 mg, Aldrich, CAS No. 112-96-9) was dissolved in 5 mL of N,N'-dimethylformamide (DMF) and was added to a solution of unprotected IB5 peptide having a cysteine residue added to the C-terminus, given as SEQ ID NO:52, (150 mg) dissolved in 10 mL of DMF. Triethylamine (30 mg) was added to catalyze the reaction. The solution was stirred at room temperature for 120 h. The solvent was evaporated yielding 191 mg of an off-white, crystalline powder. The product was analyzed by gas chromatography-MALDI mass spectrometry and found to contain two components having molecular weights of 1717 and 2013 g/mol, consistent with 1 and 2 octadecyl units respectively, covalently attached to the peptide.

Hair Coloring:

The octadecyl-hair-binding peptide conjugate (28 mg) was added to 10 g of a 0.5 wt % stock solution of Basic Violet #2 (Aldrich, Milwaukee, Wis.; CAS 3248-91-7) in water and the solution was allowed to stir overnight. A natural white hair swatch (International Hair Importers & Products Inc., Bellerose, N.Y.) was inserted into a 13 mm×100 mm test tube and 8 mL of the conjugate/dye mixture was injected into the test tube. The hair swatch was stirred in contact with the colorant solution for 30 min using a magnetic stirrer; then was removed and air dried for 30 min.

The hair swatch was then subjected to a water rinse using copious amounts of deionized water, followed by eight shampoo treatments over a period of several days. The shampoo treatment involved the application of a commercially available shampoo, Pantene Pro-V Sheer Volume (Proctor & Gamble, Cincinnati, Ohio), to the hair as follows. A quarter-sized drop of the shampoo was distributed evenly over the hair swatch and then was massaged aggressively into the hair for 30 sec, after which the hair swatch was rinsed with water to remove the shampoo. The hair swatch was then dried at room temperature.

The procedure described above was repeated without the addition of the conjugate sealant to serve as a control. Color durability was rated qualitatively using visual observation of color retention against the control using the scale described in Example 1.

After the shampoo treatment, the color of the hair swatch treated with the dye and the octadecyl-hair-binding peptide sealant was evaluated to be "good" indicating that there was a large improvement in color retention compared to the control.

Example 4

Coloring Hair Using a Mixture of Different Hair-Binding Peptides as Sealant The purpose of this Example was to demonstrate the coloring of hair using a hair dye in combination with a mixture of two different hair-binding peptides as a sealant. A mixture of two different single copy hair-binding peptides was used.

The hair-binding peptides used in this Example were IB5 having a cysteine residue added to the C-terminus, given as SEQ ID NO:52, and KF11, given as SEQ ID NO:2, both of which were obtained from SynPep. Each of the peptides was used at a concentration of 0.125 wt %. The procedure described in Example 1 was used with a Basic Violet #2 concentration of 0.50 wt % except that eight shampoo washes were performed instead of the five shampoo washes used in Example 1.

After the shampoo treatment, the color of the hair swatch treated with the dye and the mixture of hair-binding peptides was evaluated to be "very good" indicating that there was minimal colorant loss after shampoo treatment. The control without the hair-binding peptide showed significant color loss after the shampoo treatment. These results indicate that hair color retention may be improved by using a mixture of different hair-binding peptides.

This experiment was repeated using a mixture of hair-binding peptide KF11 (SEQ ID NO:2) and the empirically generated peptide used in Example 2 (SEQ ID NO:8). With these two peptides there was no improvement in the color retention after shampoo treatment compared to the control. This result suggests that when using a mixture of two different hair-binding peptides, care must be taken to ensure that there is no interaction between the peptides that mitigates the beneficial effect. It is believed that the highly polar empirically generated peptide interacted with the KF11 peptide, thereby eliminating the sealant effect.

Example 5

Biological Production of a Multi-Copy Hair-Binding Peptide

The purpose of this Example was to prepare the multi-copy hair-binding peptide HC77607, given as SEQ ID NO:16 using recombinant DNA and molecular cloning techniques. The multi-copy hair-binding peptide was comprised of six hair-binding peptide sequences separated by peptide spacers, 3 copies each of KF11 (SEQ ID NO:2) and D21' (SEQ ID NO:3). The peptide was expressed in *E. coli* as inclusion bodies. Additional amino acid sequences (i.e., peptide tags) were fused to the multi-copy hair-binding peptide sequence in order to promote inclusion body formation.

Construction of the HC77607 Gene:

A DNA sequence encoding the amino acid sequence of peptide HC77607, which is given as SEQ ID NO:16, was designed by GenScript Corp. (Scotch Plains, N.J.) using proprietary back-translation algorithms that optimized codon usage for high-level expression in *E. coli* and avoided repetitive sequences and RNA secondary structure. The coding DNA sequence is given as SEQ ID NO:23. In this coding sequence, a recognition site for endonuclease BamHI was included at the N-terminus, and two termination codons plus recognition sites for endonucleases AscI and HindIII were appended at the C-terminus. This coding DNA sequence was assembled from synthetic oligonucleotides and cloned in the plasmid vector pUC57 between BamHI and HindIII sites by GenScript Corp to give plasmid pUC57/HC77607. The DNA sequence was verified by GenScript Corp.

Construction of the Expression Vector pLX121:

Cloning of the Gene of TBP101 Peptide:

A 68 amino acid synthetic peptide, named TBP1 and given as SEQ ID NO:24, was designed. The gene for peptide TBP1, referred to as TBP1, was assembled from synthetic oligonucleotides (obtained from Sigma-Genosys, Woodlands, Tex.), which are given in Table 2.

TABLE 2

Oligionucleotides Used to Prepare the TBP1 Gene

| Oligo Name | Sequence | SEQ ID NO: |
|---|---|---|
| TBP1 (+) 1 | GGATCCATCGAAGGTCGTTTCCACGAAAA CTGGCCGTCTGGTGGCGGTACCTCTACT TCCAAAGCTTCCACCACTACGACTTCTAG CAAAACCACCACTACAT | 25 |
| TBP1 (+) 2 | CCTCTAAGACTACCACGACTACCTCCAAAA CCTCTACTACCTCTAGCTCCTCTACGGGCG GTGGCACTCACAAGACCTCTACTCAGCGTC TGCTGGCTGCATAA | 26 |
| TBP1 (−) 1 | TTATGCAGCCAGCAGACGCTGAGTAGAGGT CTTGTGAGTGCCACCGCCCGTAGAGGAGC TAGAGGTAGT | 27 |
| TBP1 (−) 2 | AGAGGTTTTGGAGGTAGTCGTGGTAGTCTT AGAGGATGTAGTGGTGGTTTTGCTAGAAGT CGTAGTGGT | 28 |
| TBP1 (−) 3 | GGAAGCTTTGGAAGTAGAGGTACCGCCA CCAGACGGCCAGTTTTCGTGGAAACGAC CTTCGATGGATCC | 29 |

Each oligonucleotide was phosphorylated with ATP using T4 polynucleotide kinase. The resulting oligonucleotides were mixed, boiled for 5 min, and then cooled to room temperature slowly. Finally, the annealed oligonucleotides were ligated with T4 DNA ligase to give synthetic DNA fragment TBP1, given as SEQ ID NO:30, which encodes the TBP101 peptide.

Construction of pINK1 Expression Plasmid:

TBP1 was integrated into the Gateway™ Technology system for protein over-expression (Invitrogen, Carlsbad, Calif.) according the manufacturer's instructions. In the first step, the TBP1 ligation mixture was used in a PCR reaction catalyzed by pfu DNA polymerase (Stratagene, La Jolla, Calif.), following the standard PCR protocol. Primer 5'TBP1 (5'-CAC CGG ATC CAT CGA AGG TCG T-3'), given as SEQ ID NO:31, and primer 3'TBP1 (5'-TCA TTA TGC AGC CAG CAG CGC-3'), given as SEQ ID NO:32, were used for amplification of the TBP1 fragment. Due to the design of these primers, an additional sequence of CACC and another stop codon TGA were added to the 5' and 3' ends of the amplified fragments.

The amplified TBP1 was directly cloned into pENTR/D-TOPO vector using Invitrogen's pENTR directional TOPO® cloning kit, resulting in Gateway entry plasmid pENTR-TBP1. This entry plasmid was propagated in One Shot TOP10 E. coli strain (Invitrogen). The accuracy of the PCR amplification and cloning were determined by DNA sequencing at the DuPont Sequencing Facility.

Plasmid pENTR-TBP1 was further modified by site directed mutagenesis using Stratagene's QuickChange® II Site-Directed Mutagenesis Kit (Stratagene La Jolla, Calif.; catalog no. 200523), following the manufacturer's instructions, to create recognition sites for endonucleases NgoMI (GCCGGC) and KasI (GGCGCC). To create recognition sites for endonuclease NgoMI, primer AGG-1-F, given as SEQ ID NO:33, and primer AGG-1-R, given as SEQ ID NO:34, were used in the mutagenesis. To create a KasI site, primer GGA-1-F, given as SEQ ID NO:35, and primer GGS-1-R, given as SEQ ID NO:36, were used in the mutagenesis.

The mutagenesis resulted in plasmid pENTR-TBP101, which encoded a 68-amino acid synthetic peptide, named TBP101, given as SEQ ID NO:37.

Finally, the entry plasmid was mixed with pDEST17. LR recombination reactions were catalyzed by LR Clonase™ (Invitrogen). The destination plasmid, pINK101 was constructed and propagated in the DH5alpha E. coli strain. The accuracy of the recombination reaction was determined by DNA sequencing. All reagents for LR recombination reactions were provided in Invitrogen's E. coil expression system with Gateway™ Technology kit.

The resulting plasmid contained the coding region 6H-TBP1 for recombinant protein INK101, which is an 11.6 kDa protein. This protein sequence includes a 6xHis tag and a peptide linker that includes a Factor Xa recognition site before the sequence of the TBP101 peptide. The coding region for INK101, between the restriction sites NdeI and AscI, is given as SEQ ID NO:38.

The region coding for the 6xHis tag and following linker (28-aa) can be excised from pINK101 by digestion with the NdeI and BamHI restriction enzymes.

To test the expression of the 6H-TBP1 coding sequence, the expression plasmid pINK101 was transformed into the BL21-AI E. coli strain (Invitrogen catalog no. C6070-03). To produce the recombinant protein, 50 mL of LB-ampicillin broth (10 g/L bacto-tryptone, 5 g/L bacto-yeast extract, 10 g/L NaCl, 100 mg/L ampicillin, pH 7.0) was inoculated with one colony of the transformed bacteria and the culture was shaken at 37° C. until the $OD_{600}$ reached 0.6. The expression was induced by adding 0.5 mL of 20% L-arabinose to the culture and shaking was continued for another 4 h. Analysis of the cell protein by polyacrylamide gel electrophoresis demonstrated the production of the TBP101 peptide.

Introduction of a DP Cleavage Site in the Amino Acid Sequence of TBP101:

The DP peptide bond, which is particularly labile at low pH (M. Landon, *Methods Enzymol.* 47:145-9 (1977)), was used as an acid cleavage site to separate the peptide to be produced from the stabilizing tag. Thus, the amino acid sequence of TBP101, given as SEQ ID NO:37, was altered to include an acid-labile DP sequence between the upstream linker-coded region and the TBP101 sequence to give TBP101-DP, given as SEQ ID NO:39.

The sequence of the plasmid pINK101 was modified by site-directed mutagenesis to change two codons encoding the EG dipeptide sequence into codons encoding the DP dipeptide at the beginning of the 6H-TBP1 gene. The DP acid cleavage site was added using Stratagen's QuickChange® II Site-Directed Mutagenesis Kit (Stratagene La Jolla, Calif.; catalog no. 200523) following the manufacturer's instructions. The oligonucleotides used to perform the site-directed mutagenesis are given as SEQ ID NO:40 (top strand) and SEQ ID NO:41 (bottom strand).

The resulting plasmid was transformed into chemically competent TOP 10 cells (Invitrogen; catalog no. C4040-06). Plasmid DNA was prepared using the QIAprep Spin Miniprep kit (QIAGEN, Valencia, Calif.) and the site-directed mutations were confirmed by sequencing. Amino acids at position 32 and 33 of TBP101, glutamic acid (E) and glycine (G), were changed to aspartic acid (D) and proline (P), respectively by changing four nucleotide residues (GM to GAT and GGT to CCA). The resulting plasmid, referred to as pINK101-DP, is given as SEQ ID NO:42.

The production of peptide from plasmid pINK101-DP was assessed as described above. pINK101-DP like the parental pINK101 plasmid led to the production of insoluble peptide in the form of inclusion bodies.

Design of Tag IBT3:

A DNA sequence encoding a peptide having a sequence given as SEQ ID NO:43 and referred to as IBT3, was assembled from two synthetic oligonucleotides (Sigma Genosys), given as SEQ IN NOs:44 and 45, with complementary sequence. Overhangs were included in each oligonucleotide to generate cohesive ends that were compatible with the restriction site NdeI and BamHI. The two oligos were annealed by heating a mixture of the oligos (100 pmol each in deionized water) at 99° C. for 10 min and then allowing the mixture to cool slowly to room temperature.

The plasmid pINK101-DP was digested in Buffer 2 (New England Biolabs, Beverly, Mass.) with the NdeI and BamHI restriction enzymes (New England Biolabs Beverly, Mass.) to release a 90 bp fragment corresponding to the 6xHis tag and the linker from the parental pDEST17 plasmid that includes the att site of the gateway cloning system. The NdeI-BamHI fragments from the digested plasmid were separated by agarose gel electrophoresis and the vector was purified using the Qiagen QIAquick® Gel Extraction Kit (QIAGEN; catalog no. 28704). The diluted annealed oligos (approximately 0.2 pmol) were ligated with T4 DNA Ligase (New England Biolabs; catalog no. M0202) to the NdeI-BamHI digest, gel purified plasmid (approximately 50 ng) at 12° C. for 18 h. Plasmid DNA isolated from $E. coli$ TOP10 transformants was analyzed and the sequence of the expected plasmid was confirmed by sequencing. This plasmid, designated as pLX121, encodes a peptide called IBT3-TBP101. The completed, sequence-confirmed construct was tested for expression as outlined above.

Construction of KSI (EP,S) Fusion Partner:

The commercially available plasmid vector pET-31b(+) (Novagen/EMD Biosciences, Madison, Wis.) provides sequences coding for a fragment of the enzyme ketosteroid isomerase (KSI). This fragment of KSI tends to form insoluble inclusion bodies in $E, coli$ when fused to peptides of interest. In order to adapt this fusion partner sequence, a KSI fragment was amplified by PCR by using the plasmid pET-31b(+) as template and the oligonucleotide primers given as SEQ ID NOs:46 and 47.

The resulting PCR product was digested with endonucleases NdeI and BamHI and cloned into plasmid pLX121, also digested with NdeI and BamHI, in $E. coli$ DH10B. The final construct was designated KSI-101 DP and the plasmid containing it was designated pINK101_DP_KSI.

The plasmid pINK101_DP_KSI was then modified by site-directed mutagenesis (QuickChange; Stratagene) to remove an acid-labile DP sequence from the KSI protein product, changing it to EP, and to remove the only C residue in the KSI sequence, changing it to S, at the same time. For this purpose, two pairs of oligos, given as SEQ ID NOs:48 and 49 and SEQ ID NO:s50 and 51, were used simultaneously. The resulting plasmid was designated pINK101_DP_KSI(EP,S).

Construction of the KSI-HC77607 and KSI(EPS)-HC77607 Gene Fusions:

The DNA plasmids pINK101_DP_KSI and pINK101_DP_KSI(EP,S) were digested with endonucleases BamHI and Ascl, and the fragment encoding TBP101 was replaced by a BamHI-Ascl fragment encoding HC77607, derived from plasmid pUC57/HC77607 (described above). The resulting plasmids encode KSI-HC77607 and KSI(EP,S) fusion proteins operably linked to the T7 gene 10 promoter. These plasmids were first cloned in the non-expressing strain $E. coli$ TOP10, then transferred to the expressing strain, $E. coli$ BL21-Al.

Fermentation:

The recombinant $E. coli$ strain, described above, was grown in a 6-L fermentation, which was run in batch mode initially, and then in fed-batch mode. The composition of the fermentation medium is given in Table 3. The pH of the fermentation medium was 6.7. The fermentation medium was sterilized by autoclaving, after which the following sterilized components were added: thiamine hydrochloride (4.5 mg/L), glucose (22.1 g/L), trace elements, see Table 4 (10 mL/L), ampicillin (100 mg/L), and inoculum (seed) (125 mL). The pH was adjusted as needed using ammonium hydroxide (20 vol %) or phosphoric acid (20 vol %). The added components were sterilized either by autoclaving or filtration.

TABLE 3

Composition of Fermentation Medium

| Component | Concentration |
|---|---|
| $KH_2PO_4$ | 9 g/L |
| $(NH_4)_2HPO_4$ | 4 g/L |
| $MgSO_4 \cdot 7H_2O$ | 1.2 g/L |
| Citric Acid | 1.7 g/L |
| Yeast extract | 5.0 g/L |
| Mazu DF 204 Antifoam | 0.1 mL/L |

TABLE 4

Trace Elements

| Component | Concentration, mg/L |
|---|---|
| EDTA | 840 |
| $CoCl_2 \cdot H_2O$ | 250 |
| $MnCl_2 \cdot 4H_2O$ | 1500 |
| $CuCl_2 \cdot 2H_2O$ | 150 |
| $H_3BO_3$ | 300 |
| $Na_2MoO_4 \cdot 2H_2O$ | 250 |
| $Zn(CH_3COO)_2 \cdot H_2O$ | 1300 |
| Ferric citrate | 10000 |

The operating conditions for the fermentation are summarized in Table 5. The initial concentration of glucose was 22.1 g/L. When the initial residual glucose was depleted, a pre-scheduled, exponential glucose feed was initiated starting the fed-batch phase of the fermentation run. The glucose feed (see Tables 6 and 7) contained 500 g/L of glucose and was supplemented with 5 g/L of yeast extract. The components of the feed medium were sterilized either by autoclaving or filtration. The goal was to sustain a specific growth rate of 0.13 $h^{-1}$, assuming a yield coefficient (biomass to glucose) of 0.25 g/g, and to maintain the acetic acid levels in the fermentation vessel at very low values (i.e., less than 0.2 g/L). The glucose feed continued until the end of the run. Induction was initiated with a bolus of 2 g/L of L-arabinose at the selected time (i.e., 15 h of elapsed fermentation time). A bolus to deliver 5 g of yeast extract per liter of fermentation broth was added to the fermentation vessel at the following times: 1 h prior to induction, at induction time, and 1 h after induction time. The fermentation run was terminated after 19.97 h of elapsed fermentation time, and 4.97 h after the induction time.

TABLE 5

Fermentation Operating Conditions

| Condition | Initial | Minimum | Maximum |
|---|---|---|---|
| Stirring | 220 rpm | 220 rpm | 1200 rpm |
| Air Flow | 3 SLPM | 3 SLPM | 30 SLPM |
| Temperature | 37° C. | 37° C. | 37° C. |
| pH | 6.7 | 6.7 | 6.7 |
| Pressure | 0.500 atm (50.7 kPa) | 0.500 atm (50.7 kPa) | 0.500 atm (50.7 kPa) |
| Dissolved $O_2$* | 20% | 20% | 20% |

*Cascade stirrer, then air flow.

TABLE 6

Composition of Feed Medium

| Component | Concentration |
|---|---|
| $MgSO_4 \cdot 7H_2O$ | 2.0 g/L |
| Glucose | 500 g/L |
| Ampicillin | 150 mg/L |
| $(NH_4)_2HPO_4$ | 4 g/L |
| $KH_2PO_4$ | 9 g/L |
| Yeast extract | 5.0 g/L |
| Trace Elements - Feed (Table 7) | 10 mL/L |

TABLE 7

Trace Elements - Feed

| Component | Concentration, mg/L |
|---|---|
| EDTA | 1300 |
| $CoCl_2 \cdot H_2O$ | 400 |
| $MnCl_2 \cdot 4H_2O$ | 2350 |
| $CuCl_2 \cdot 2H_2O$ | 250 |
| $H_3BO_3$ | 500 |
| $Na_2MoO_4 \cdot 2H_2O$ | 400 |
| $Zn(CH_3COO)_2 \cdot H_2O$ | 1600 |
| Ferric citrate | 4000 |

Isolation and Purification of Peptide HC77607:

After completion of the fermentation run, the entire fermentation broth was passed three times through an APV model 2000 Gaulin type homogenizer at 12,000 psi (82,700 kPa). The broth was cooled to below 5° C. prior to each homogenization. The homogenized broth was immediately processed through a Westfalia WhisperFuge™ (Westfalia Separator Inc., Northvale, N.J.) stacked disc centrifuge at 600 mL/min and 12,000 RCF to separate inclusion bodies from suspended cell debris and dissolved impurities. The recovered paste was re-suspended at 15 g/L (dry basis) in water and the pH adjusted to 10.0 using NaOH. The suspension was passed through the APV 2000 Gaulin type homogenizer at 12,000 psi (82,700 kPa) for a single pass to provide rigorous mixing. The homogenized pH 10 suspension was immediately processed in a Westfalia WhisperFuge™ stacked disc centrifuge at 600 mL/min and 12,000 RCF to separate the washed inclusion bodies from suspended cell debris and dissolved impurities. The recovered paste was resuspended at 15 gm/L (dry basis) in pure water. The suspension was passed through the APV 2000 Gaulin type homogenizer at 12,000 psi (82,700 kPa) for a single pass to provide rigorous washing. The homogenized suspension was immediately processed in a Westfalia WhisperFuge™ stacked disc centrifuge at 600 mL/min and 12,000 RCF to separate the washed inclusion bodies from residual suspended cell debris and NaOH.

The recovered paste was resuspended in pure water at 25 g/L (dry basis) and the pH of the mixture was adjusted to 2.2 using HCl. Dithiothreitol (DTT, 10 mM) was added to break disulfide bonds. The acidified suspension was heated to 70° C. for 14 h to complete cleavage of the DP site separating the fusion peptide from the product peptide. The product was cooled to 5° C. and held for 12 h. The mixture was centrifuged at 9000 RCF for 30 min and the supernatant was decanted. The supernatant was then filtered with a 0.2 μm membrane.

The filtered product was loaded in a 22×250 mm reverse phase chromatography column containing 10 μm C18 media which was preconditioned with 10% acetonitrile, 90% water with 0.1 vol % trifluoroacetic acid (TFA). The product was recovered in a purified state by eluting the column with a gradient of water and acetonitrile, ramping from 10% to 25% acetonitrile in water with TFA at 0.1 vol %. The eluent containing the product peptide was collected and concentrated by vacuum evaporation by a factor of 2:1 before lyophilization. Spectrophotometric detection at 220 nm was used to monitor and track elution of the product peptide.

Example 6

Coloring Hair Using a Multi-Copy Hair-Binding Peptide as Sealant

The purpose of this Example was to demonstrate the coloring of hair using a hair dye in combination with a multi-copy hair-binding peptide as a sealant. The multi-copy hair-binding peptide used in this Example was prepared as described in Example 5.

Hair Coloring:

This multi-copy hair-binding peptide, given as SEQ ID NO:16, (28 mg) was added to 10 g of a 0.5 wt % stock solution of Basic Violet #2 (Aldrich, Milwaukee, Wis.; CAS 3248-91-7) in water and the solution was allowed to stir overnight. A natural white hair swatch (International Hair Importers & Products Inc., Bellerose, N.Y.) was inserted into a 13 mm×100 mm test tube and 8 mL of the peptide/dye mixture was injected into the test tube. The hair swatch was stirred in contact with the colorant solution for 30 min using a magnetic stirrer; then was removed and air dried for 30 min.

The hair swatch was then subjected to a water rinse using copious amounts of deionized water, followed by eight shampoo treatments over a period of several days. The shampoo treatment involved the application of a commercially available shampoo, Pantene Pro-V Sheer Volume (Proctor & Gamble, Cincinnati, Ohio), to the hair as follows. A quarter-sized drop of the shampoo was distributed evenly over the hair swatch and then was massaged aggressively into the hair for 30 sec, after which the hair swatch was rinsed with water to remove the shampoo. The hair swatch was then dried at room temperature.

The procedure described above was repeated without the addition of the hair-binding peptide sealant to serve as a control. Color durability was rated qualitatively using visual observation of color retention against the control using the scale described in Example 1.

After the shampoo treatment, the color of the hair swatch treated with the dye and the multi-copy hair-binding peptide sealant was evaluated to be "very good" indicating that there was minimal color loss.

Examples 7-12

Coloring Hair Using Hair-Binding Peptides as Sealant

The purpose of these Examples was to demonstrate the coloring of hair using a hair dye in combination with various hair-binding peptides as a sealant. The color retention was quantified using a spectrophotometic measurement technique.

Hair coloring was performed as described in Example 1 using Red Dye No. 33 (CAS No. 3567-66-6, obtained from Abbey Color, Philadelphia, Pa.) at a concentration of 0.07 wt %. Various hair-binding peptides were used, as listed in Table 8. After the hair was colored, it was rinsed once with deionized, and then given one shampoo treatment, as described in Example 1.

The color intensity after the shampoo was measured using a X-Rite® SP78™ Sphere Spectrophotometer (X-Rite, Inc., Grandville, Mich.), by placing the colored hair sample into the photosensor and calculating L*, a* and b* parameters representing the photometer response. An initial baseline L* value was measured for the uncolored hair and all measurements were the average of three individual determinations. Delta E values were calculated using equation 1 below:

$$\text{Delta } E = ((L^*_1 - L^*_2)^2 + (a_1 - a_2)^2 + (b_1 - b_2)^2)^{1/2} \quad (1)$$

where L*=the lightness variable and a* and b* are the chromaticity coordinates of CIELAB colorspace as defined by the International Commission of Illumination (CIE) (Minolta, *Precise Color Communication—Color Control From Feeling to Instrumentation*, Minolta Camera Co., 1996). Larger Delta E value are indicative of better color retention. The results are summarized in Table 8.

TABLE 8

Results of Color Retention After Shampoo Treatment

| Example | Peptide | SEQ ID NO: | Peptide Conc. wt % | Delta E |
|---------|---------|------------|--------------------|---------|
| 7 | A09 | 5 | 0.95% | 34.8 |
| 8 | A09 | 5 | 0.25% | 25.6 |
| 9 | HC77607 | 16 | 0.25% | 19.8 |
| 10 | IB5-Cys | 52 | 0.25% | 20.4 |
| 11, Comparative | Random | 22 | 0.25% | 10.8 |
| 12, Comparative | None | — | — | 8.09 |

As can be seen from the results in Table 8, the use of a hair-binding peptide as a sealant for the dye provided significantly better hair color retention, as measured by the Delta E values, than the use of the dye alone (Example 12) or the use of a random peptide as a sealant Example 11).

Example 13

Coloring Hair Using a Mixture of Different Hair-Binding Peptides as Sealant

The purpose of this Example was to demonstrate the coloring of hair using a hair dye in combination with a mixture of two different hair-binding peptides as a sealant. A mixture of a single copy hair-binding peptide and a multi-copy hair-binding peptide was used.

The hair-binding peptides used in this Example were IB5 having a cysteine residue added to the C-terminus, given as SEQ ID NO:52, obtained from SynPep, and the multi-copy hair-binding peptide HC77607, given as SEQ ID NO:16, prepared as described in Example 5. Each of the peptides was used at a concentration of 0.125 wt %. The procedure described in Example 4 was used with a Basic Violet #2 concentration of 0.50wt %

After the shampoo treatment, which consisted of 8 shampoo washes, the color of the hair swatch treated with the dye and the mixture of hair-binding peptides was evaluated to be "very good" indicating that there was minimal colorant loss after shampoo treatment. The control without the hair-binding peptide showed significant color loss after the shampoo treatment. These results indicate that hair color retention may be improved by using a mixture of different hair-binding peptides.

What is claimed is:

1. A method for applying a benefit agent to hair comprising the steps of:
   a) providing a hair benefit agent having affinity to hair;
   b) providing a composition comprising a hair-binding peptide wherein said peptide comprise from about 7 to about 50 amino acids and wherein at least about 40 mole % are positively charged amino acids;
   c) applying the benefit agent and the composition comprising a hair-binding peptide to hair for a time sufficient for the hair benefit agent and the hair-binding peptide to bind to hair.

2. A method according to claim 1 wherein the hair benefit agent is selected from the group consisting of hair colorants and hair conditioners.

3. A method according to claim 2 wherein the hair colorant is selected from the group consisting of dyes, pigments and nanoparticles.

4. A method according to claim 3 wherein the dye is selected from the group consisting of 4-hydroxypropylamino-3-nitrophenol, 4-amino-3-nitrophenol, 2-amino-6-chloro-4-nitrophenol, 2-nitro-paraphenylenediamine, N,N-hydroxyethyl-2-nitro-phenylenediamine, 4-nitro-indole, 2-nitro-5-glyceryl methylaniline, 3-methylamino-4-nitrophenoxyethanol, 3-nitro-p-hydroxyethylaminophenol, hydroxyanthraquinoneaminopropylmethyl morpholinium methosulfate, Henna, HC Blue 1, HC Blue 2, HC Yellow 4, HC Red 3, HC Red 5, HC Red 7, HC Violet 1, HC Violet 2, HC Blue 7, HC Blue 10, HC Blue 12, HC Yellow 2, HC Yellow 6, HC Yellow 8, HC Yellow 12, HC Orange 2, HC Orange 3, HC Brown 2, D&C Yellow 1, D&C Yellow 3, D&C Blue 1, Disperse Blue 3, Disperse Violet 1, Disperse Orange, Disperse Violet 4, Disperse Black 9, Basic Orange 31, Basic Yellow 57, Basic Yellow 87, HC Yellow No. 9, Basic Blue 26, Basic Blue 7, Basic Blue 99, Basic Violet 14, Basic Violet 2, Basic Brown 16, Basic Brown 17, Basic Red 2, Basic Red 51, Acid Red 33, Brilliant Black 1, eosin derivatives, and halogenated fluorescein derivatives.

5. A method according to claim 3 wherein the wherein the pigment is selected from the group consisting of D&C Red No. 36, D&C Red No. 30, D&C Orange No. 17, Green 3 Lake, Ext. Yellow 7 Lake, Orange 4 Lake, Red 28 Lake, the calcium lakes of D&C Red Nos. 7, 11, 31 and 34, the barium lake of D&C Red No. 12, the strontium lake D&C Red No. 13, the aluminum lakes of FD&C Yellow No. 5 and No. 6, the aluminum lakes of FD&C No. 40, the aluminum lakes of D&C Red Nos. 21, 22, 27, and 28, the aluminum lakes of FD&C Blue No. 1, the aluminum lakes of D&C Orange No. 5, the aluminum lakes of D&C Yellow No. 10; the zirconium lake of D&C Red No. 33, Cromophthal® Yellow, Sunfast® Magenta, Sunfast® Blue, iron oxides, calcium carbonate, aluminum hydroxide, calcium sulfate, kaolin, ferric ammonium ferrocyanide, magnesium carbonate, carmine, barium sulfate, mica, bismuth oxychloride, zinc stearate, manganese violet, chromium oxide, titanium dioxide, titanium dioxide nanoparticles, zinc oxide, barium oxide, ultramarine blue, bismuth citrate, hydroxyapatite, zirconium silicate, and carbon black particles.

6. A method according to claim 3 wherein the nanoparticles are colored polymer nanoparticles comprised of materials selected from the group consisting of polystyrene, polymethyl methacrylate, polyvinyltoluene, styrene/butadiene copolymer, and latex.

7. A method according to claim 2 wherein the hair conditioner is selected from the group consisting of cationic polymers, cationic surfactants, fatty alcohols, fatty amines, nonionic polymers, silicones, siloxanes, polymer emulsions, and nanoparticles.

8. A method according to claim 1 wherein the hair benefit agent and the composition comprising a hair-binding peptide are applied to the hair concomitantly.

9. A method according to claim 1 wherein the hair benefit agent is applied to the hair prior to the application of the composition comprising a hair-binding peptide.

10. A method according to claim 1 wherein the composition comprising a hair-binding peptide is applied to the hair prior to the application of the hair benefit agent.

11. A method according to claim 1 wherein the composition comprising the hair-binding peptide comprises a conjugate further comprising the hair-binding peptide coupled to the hair benefit agent.

12. A method according to claim 11 wherein the hair benefit agent is selected from the group consisting of hair colorants and hair conditioners.

13. A method according to claim 11 wherein the hair-binding peptide of the conjugate is covalently bonded to the benefit agent.

14. A method according to claim 1 wherein the hair benefit agent of step (a) is optionally coupled to a hair-binding peptide.

15. A method according to claim 1 wherein the hair-binding peptide is generated combinatorially by a process selected from the group consisting of phage display, yeast display, bacteria display and combinatorial solid phase peptide synthesis.

16. A method according to claim 1 wherein the hair-binding peptide is generated empirically.

17. A method according to claim 16 wherein the empirically generated peptide comprises positively charged amino acids having affinity for hair.

18. A method according to claim 1 further comprising the step of:
   d) reapplying the composition comprising a hair-binding peptide to the hair for a time sufficient for the hair-binding peptide to bind to hair.

19. The method of claim 1, wherein the hair binding peptide is from about 7 amino acids to about 25 amino acids.

20. The method of claim 1, wherein the hair binding peptide is from about 7 amino acids to about 20 amino acids.

* * * * *